(12) United States Patent
Park et al.

(10) Patent No.: US 11,105,813 B2
(45) Date of Patent: Aug. 31, 2021

(54) METHOD FOR TARGET PROTEIN IDENTIFICATION USING THERMAL STABILITY SHIFT-BASED FLUORESCENCE DIFFERENCE IN TWO-DIMENSIONAL GEL ELECTROPHORESIS

(71) Applicant: Spark Biopharma, Inc., Seoul (KR)

(72) Inventors: Seung Bum Park, Seoul (KR); Han Kum Park, Seoul (KR)

(73) Assignee: Spark Biopharma, Inc., Seoul (KR)

( * ) Notice: Subject to any disclaimer, the term of this patent is extended or adjusted under 35 U.S.C. 154(b) by 183 days.

(21) Appl. No.: 16/238,795

(22) Filed: Jan. 3, 2019

(65) Prior Publication Data

US 2019/0195886 A1    Jun. 27, 2019

Related U.S. Application Data

(63) Continuation of application No. PCT/KR2017/010044, filed on Sep. 13, 2017.

(30) Foreign Application Priority Data

Sep. 30, 2016 (KR) .................. 10-2016-0127115

(51) Int. Cl.
*G01N 33/68* (2006.01)
*G01N 27/447* (2006.01)
*G01N 33/58* (2006.01)
*C40B 30/04* (2006.01)

(52) U.S. Cl.
CPC ....... *G01N 33/6845* (2013.01); *G01N 27/447* (2013.01); *G01N 27/44778* (2013.01); *G01N 33/582* (2013.01); *G01N 33/6803* (2013.01); *G01N 33/6842* (2013.01); *C12Y 207/11013* (2013.01); *C40B 30/04* (2013.01); *G01N 2500/04* (2013.01); *G01N 2550/00* (2013.01)

(58) Field of Classification Search
CPC ........... G01N 33/6803; G01N 33/6842; G01N 27/447; G01N 33/582; G01N 27/44778; G01N 33/6845; G01N 2550/00; G01N 2500/04; G01N 27/44773; C12Y 207/11013; C40B 30/04
See application file for complete search history.

(56) References Cited

FOREIGN PATENT DOCUMENTS

KR          10-0857592 B1     9/2008
KR     10-2014-0033366 A     11/2013
KR          10-1427328 B1     7/2014

OTHER PUBLICATIONS

Lee et al. Target identification for biologically active small molecules using chemical biology approaches. Arch. Pharm. Res. 2016, vol. 39, pp. 1193-1201. (Year: 2016).*
Lomenick et al. Identification of direct protein targets of small molecules. ACS Chemical Biology 2010, vol. 6, No. 1, pp. 34-46. (Year: 2010).*
Park, J. et al., "Discovery and Target Identification of an Antiproliferative Agent in Live Cells Using Flourescence Difference in Two-Dimensional Gel Electrophoresis", Angew. Chem. (2012) 124, 5543-5547.
Park, H. et al, "Label-free target identification using in-gel fluorescence difference via thermal stability shift", Chem. Sci. (2017) 8, 1127-1133.
International Search Report for International Patent Application No. PCT/KR2017/010044, dated Dec. 20, 2017, 2 pages.

* cited by examiner

*Primary Examiner* — Shafiqul Haq
(74) *Attorney, Agent, or Firm* — Nelson Mullins Riley & Scarborough LLP; Kongsik Kim, Esq.

(57) ABSTRACT

The present invention relates to a method for identifying a target protein using a thermal stability shift-based fluorescence difference in two-dimensional gel electrophoresis, and more specifically, a method for identifying a protein, which is a target of a specific drug, by analyzing, by means of a fluorescence difference in two-dimensional gel electrophoresis, a thermal stability shift in the protein when a specific drug, preferably a bioactive molecule, binds to the target protein.

13 Claims, 19 Drawing Sheets

METHOD FOR TARGET PROTEIN IDENTIFICATION USING THERMAL STABILITY SHIFT-BASED FLUORESCENCE DIFFERENCE IN TWO-DIMENSIONAL GEL ELECTROPHORESIS

CROSS-REFERENCE TO RELATED APPLICATIONS

This application is a continuation application of International Application No. PCT/KR2017/010044 filed on Sep. 13, 2017, which claims priority to Korean Application No. 10-2016-0127115 filed on Sep. 30, 2016. The applications are incorporated herein by reference.

TECHNICAL FIELD

The present invention relates to a method for identifying a target protein using a thermal stability shift-based fluorescence difference in two-dimensional gel electrophoresis, and more specifically, a method for identifying a protein, which is a target of a specific drug, by analyzing, by means of a fluorescence difference in two-dimensional gel electrophoresis, a thermal stability shift in the protein when a specific drug, preferably a bioactive molecule, binds to the target protein.

BACKGROUND ART

In order for small molecules to exert their biological activities, they should bind to their biomolecular partners. This event is known as target engagement, which is an important aspect of drug discovery and chemical biology research. The target proteins of traditional natural products or hit compounds from phenotypic screening are unknown in most cases. Therefore, target proteins should be identified to determine the mechanisms of action of bioactive small molecules for the development of novel therapeutic agents or research tools in biomedical sciences.

The most commonly used approach for target identification is the affinity chromatography-pull down assay (Schenone et al., *Nat. Chem. Biol.* 2013., 9, pp. 232-240). A physiological active compound is attached on agarose beads while cell lysates are incubated with beads. The target proteins bound to modified beads are separated from other proteins not bound. The recent two approaches in chemical proteomics includes (i) activity-based proteome profiling using an enzyme activity of a protein class, specifically, using a covelent bond labelling on an active site (Simon et al., *Nat. Chem. Biol.* 2013., 9, pp. 200-205) and (ii) affinity-based proteome profiling using a bond interaction of non-enzyme protein, specifically, using photoaffinity-based covalent cross-linking (Pan et al., *Nat. Prod. Rep.* 2015. 8. 24., doi:10.1039/c5np00101c). While the approaches successfully extended the range of chemical proteomics, chemical modification of original bioactive compounds was required to introduce functional handles such as electrophiles for the enzymatic reaction, alkyne moieties for click chemistry, or photoaffinity groups for covalent crosslinking to target proteins. As such, an effort to develop a probe for target identification has been continued by minimization of a functional change, optimalization of photoaffinity functional groups, consideration of conformational factors comprising a molecule structure and size, and the like. For example, Korean Patent No. 10-1427328 tried to identify a target protein by labelling a bioactive molecule, via a covelent bond, with a probe comprising a specific photoreactive functional troup capable of binding with a protein and a functional group for labelling a fluorescent material.

The design and synthesis for the functionalization, however, remain as major hurdles in the target identification because a great deal of effort is inevitable to synthesize numerous analogues and explore their structure—activity relationships. Even if a probe for target identification is synthesized so as to maintain its bioactivity, the non-specific interaction between a chemically modified probe and proteome of a cell is still found. Cumbersome total syntheses of complex natural products and their insufficient extraction from natural sources may not only make a chemical modification difficult, but also may abolish the biological activity of original hit compounds even by a slight modification. As an example, bryostatin 1 is difficult to be synthesized due to its 58-step total synthesis (Keck et al., *J. Am. Chem. Soc.* 133, 744-747 (2011)). Further, its chemical structure is very complex (FIG. 7a). Therefore, it is difficult to synthesize appropriately functionalized probes for the prior target identification methods. In contrast, since hordenine has a very simple structure (FIG. 13a), it is a representative natural bioactive low molecule substance incapable of chemical mofication. As such, a label-free target identification method without any structural modification is required.

In the recently reported cellular thermal stability assay (CETSA), target engagement was monitored in a label-free manner in intact cells and tissues (Martinez Molina, et al., *Science*. 2013., 341, pp. 84-87). The amount of target proteins in the soluble fraction was measured by western blot analysis after thermal denaturation. The engagement of bioactive ligands stabilized target proteins against heat denaturation and increased the melting temperature (Tm) of the protein. Given its robustness and effectiveness, CETSA has been rapidly adopted by many researchers to confirm the target engagement. For example, WO2015/145151 tried to find a biomarker in a patient resistant to a drug by using CETSA and a quantative mass spectrometry. Korean patent publication No. 10-2014-0033366 attempted to find a ligand bound to a target protein by using a thermal shift of the protein. However, in both cases, if the changes in the melting temperature resulting from the binding between the ligand and the target protein is not so big and subtle, whether to bind the ligand to the target protein is not easily detectable. Further, CETSA is not suitable for unbiased proteome-wide target identification because this method is only applicable to hypothesis-driven candidate proteins with available antibodies. In contrast, unbiased target identification methods should be developed as a requisite for phenotypic screening, leading to the successful development of first-in-class therapeutics.

Although gel-free proteomics has been favored as a result of rapidly advancing LC-MS technique, two-dimensional gel electrophoresis(2-DE) still remains an effective proteomic approach because of its affordability, robustness, and resolution. We noted that the combining a thermal stability (TS) assay with 2-DE-based FITGE (fluorescence difference in two-dimensional gel electrophoresis) technology efficiently defined protein spots with shifted thermal stability simply by distinguishing red or green spots due to fluorescence difference between Cy3 and Cy5 signals from other yellow spots.

We tried to to develop a label-free method for proteome-wide target identification using thermal stability shift-based fluorescence difference in two-dimensional gel electrophoresis (TS-FITGE) and to demonstrate the robustness and practicality of the TS-FITGE method via target identification of bioactive natural products with extreme chemical structures: a complex natural product that is difficult to be synthesized and a small and simple natural product lacking room for chemical modification. The two fluorescence signals were utilized to vidualize protein spots thermally stabilized or destabilized. The melting curves of each protein spot were plotted by analyzing the quantative image of a gel at various temperatures.

As a result, TS-FITGE method successfully revealed the known target proteins of methotrexate and bryostatin 1, especially, confirming the applicability of this method in the identification of membrane-anchored proteins. Furthermore, the unknown target protein of hordenine, a simple natural product that is a regulator of in vitro protein, was also identified and functionally validated.

SUMMARY

As such, the purpose of the present invention is to provide a method for identifying a target protein of a drug molecule, preferably, of a bioactive molecule, using a thermal stability shift-based fluorescence difference in two-dimensional gel electrophoresis (TS-FITGE).

To achieve the purpose, the present invention provides a method for identifying a target protein of a drug molecule, preferabley, of a bioactive molecule, comprising the steps of:

(a) preparing mixture A comprising cell lysates or human-derived cells;

(b) preparing mixture B comprising the mixture of cell lysates or human-derived cells, and a drug molecule;

(c) modifying the temperature of mixture A and mixture B to a specific and same temperature;

(d) mixing each of mixture A and mixture B at a specific temperature as obtained in step (c) with fluorescent materials having a different wavelength from each other, respectively, so that the proteins existed in a soluble fraction of each of mixture A and mixture B are labelled with the fluorescent materials having a different wavelength from each other, respectively;

(e) mixing mixture A and mixture B as obtained in step (d) to prepare mixture C;

(f) performing electrophoresis of mixture C; and (g) analyzing a fluorescence wavelength of a protein spot shown in a gel by the electrophoresis of step (f) to confirm a protein showing thermal stability shift resulting from step (c).

The method identifying for a target protein using TS-FITGE according to the present invention can easily find a target protein of bioactive natural products with extreme chemical structures, i.e., a complex natural product that is difficult to be synthesized and a small and simple natural product lacking room for chemical modification, even without labelling using a probe, and can be very efficient in developing an innovative new drug and treatment. In addition, the present invention can easily detect thermal stability shifts in a protein through noticeable color changes at a specific temperature even when changes in melting temperature due to thermal stability shifts in the protein are subtle or the slope of a melting curve is sharp, by combining the prior thermal stability assay with FITGE technology (see FIG. 16).

DETAILED DESCRIPTION

Figure 1:
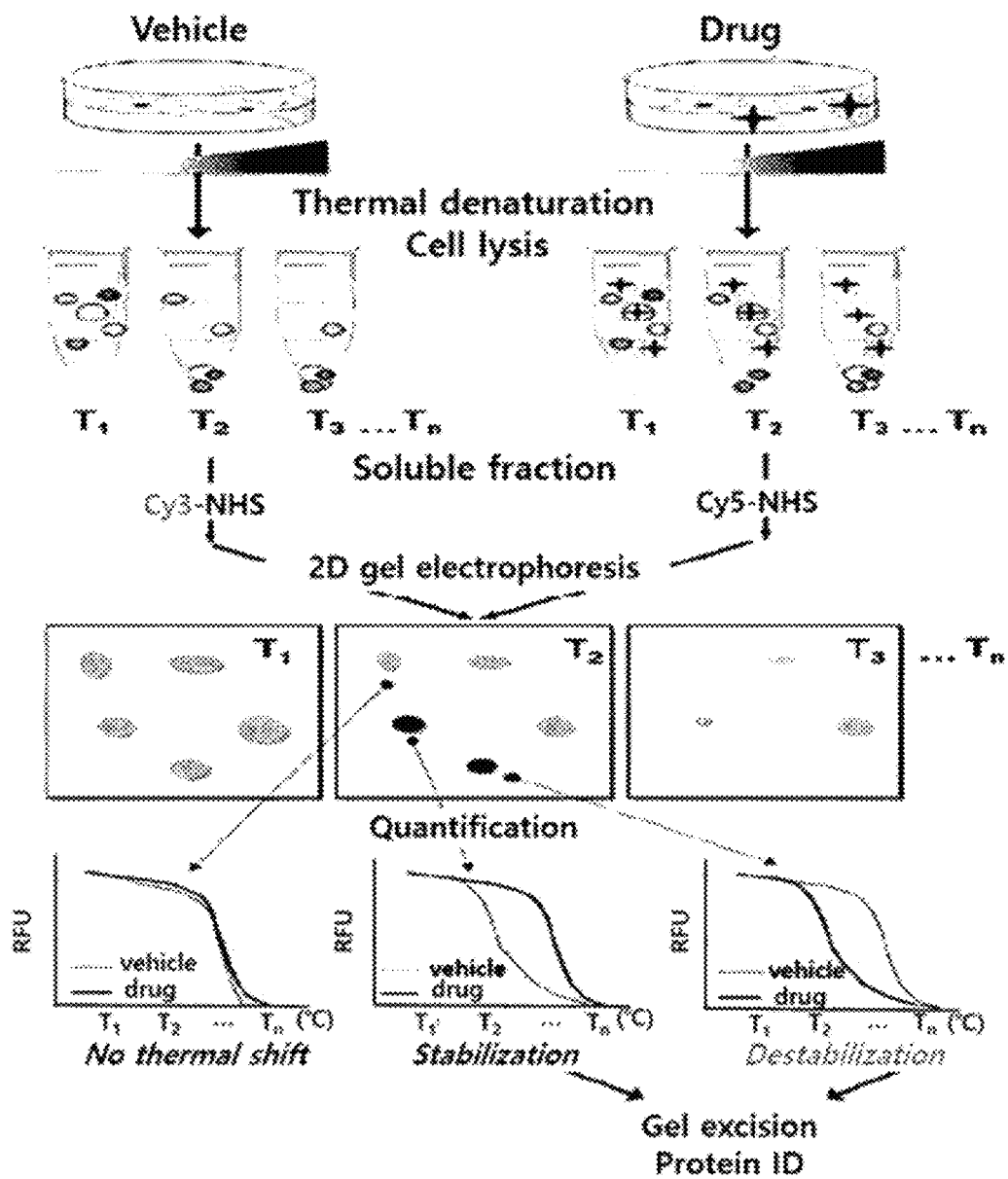
FIG. 1 is a scheme of the TS-FITGE experiment. The yellow in a microtube refers to a target protein while the crossed icon refers to a drug.

The concept "thermal stability shift" herein mans that due to the binding between a drug molecule and its target protein, (i) the target protein is thermally stabilized to have a higher Tm than the original Tm; or (ii) the target protein is thermally destabilized to have a lower Tm than the original Tm.

According to one aspect, the present invention is related to a method for identifying a target protein of a drug molecule, comprising the steps of:

(a) preparing mixture A comprising cell lysates or human-derived cells;

(b) preparing mixture B comprising the mixture of cell lysates or human-derived cells, and a drug molecule;

(c) modifying the temperature of mixture A and mixture B to a specific and same temperature;

(d) mixing each of mixture A and mixture B at a specific temperature as obtained in step (c) with fluorescent materials having a different wavelength from each other, respectively, so that the proteins existed in a soluble fraction of each of mixture A and mixture B are labelled with the fluorescent materials having a different wavelength from each other, respectively;

(e) mixing mixture A and mixture B as obtained in step (d) to prepare mixture C;

(f) performing electrophoresis of mixture C; and (g) analyzing a fluorescence wavelength of a protein spot shown in a gel by the electrophoresis of step (f) to confirm a protein showing thermal stability shift resulting from step (c).

The term "human-derived cells" means cells derived from those excreted from human, e.g., urine, face, placenta, hair, nail, etc., or those collected from human, e.g., blood, skin, tumor, tissue, etc.

According to the present invention, the specific temperature of step (c) is characterized in the range from 37 to 70° C. Further, the method is characterized in further comprising the step of plotting a melting curve graph of each protein spot in step (g).

The melting curve is a sigmoidal curve. When the protein is thermally stabilized by bonding between a drug molecule and its target protein, the sigmoidal curve is shifted to the right on the graph. When the protein is thermally destabilized, the sigmoidal curve is shifted to the left on the graph. In one example of the present invention, it was confirmed that hordenine as a bioactive molecule is bonded with nucleophosmin as a target protein to increase Tm of the protein, i.e., the thermal stabilization. In another example, it was confirmed that briostatin 1 as a bioactive molecule is bonded with PKCα as a target protein to decrease Tm of the protein, i.e., the thermal destabilization.

As such, the present invention may be characterized in that in the thermal stability shift of step (g), the protein existed in mixture B is thermally stabilized by engagement with the drug molecule. For example, when hordenine as a bioactive molecule is bonded with nucleophosmin (NPM) as a target protein, nucleophosmin is thermally stabilized. Further, the present invention may be characterized in that in the thermal stability shift of step (g), the protein existed in mixture B is thermally destabilized by engagement with the drug molecule.

For example, when bryostatin 1 as a bioactive molecule is bonded with PKCα as a target protein, PKCα is thermally destabilized.

Further, the drug molecule in step (b) is preferably a bioactive molecule, while the target protein obtained in step (g) may be, but not limited to, a membrane-anchored protein.

In the present invention, the fluorescent material of step (d) may be, but not limited to, at least one selected from the group consisting of Cy2, Cy3, Cy5, fluorescein, Alexafluor488, R6G, HEX, AlexaFluor32, TAMRA, AlexaFluor546, EtBr, SYPRO Ruby, and Blue FAM. Preferably, step (d) may be characterized in that the fluorescent material mixed with mixture A is Cy3 and the fluorescent material mixed with mixture B is Cy5. Further, preferably, an amine-reactive functional group may further be bonded to Cy3 and Cy5, respectively. Preferably, N-hydroxysuccinimide (NHS) ester may further be bonded.

<amine-reactive functional group>

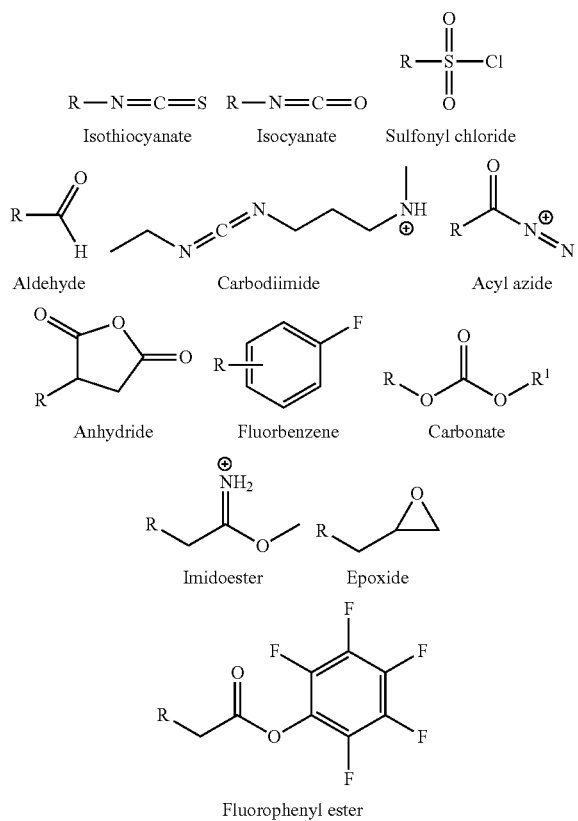

Further, in the present invention, the analysis of the fluorescence wavelength (signal) of step (g) may consist of the analysis of the ratio between the fluorescence wavelength generated from the fluorescent material labelled on the protein existed in the soluble fraction of mixture A and the fluorescence wavelength generated from the fluorescent material labelled on the protein existed in the soluble fraction of mixture B. The ratio may be calculated by a 2D gel fluorescence measuring machine generally used in the field which the present invention falls within, preferably, a DeCyder 2D software.

Further, the present invention may be characterized in that the electrophoresis of step (f) is two-dimensional (2D) gel electrophoresis. In the prior 1-dimentional (1D) electrophoresis, electrophoresis is performed to one direction to classify proteins based on molecular weight. In this case, if a protein has the molecular weight same as or similar to that of the target protein, the binding between the protein and bioactive molecule may not easily differentiated in many cases. As such, since a protein is separated in the two directions, i.e., based on molecular weight and electric charge in 2D gel electrophoresis, the problem above is solved to identify the target protein.

EXAMPLES

Hereinafter, the present invention will be described in further detail with reference to examples. It will be obvious to a person having ordinary skill in the art that these examples are for illustrative purposes only and are not to be construed to limit the scope of the present invention. The substantial scope of the present invention will be defined by the appended claims and equivalents thereof.

Proteome-Wide Target Identification Using Thermal Stability Shift

As CETSA is applicable for known candidate proteins using designated antibodies, we applied the thermal stability shift to our FITGE technique for proteome-wide target identification. As shown in FIG. 1, cells were heated at a range of temperatures for 3 minutes to induce thermal denaturation. The cells were then washed and dissolved in a phosphate-buffered saline (PBS) solution by a freeze-thawing cycle, followed by precipitating a denatured protein by centrifugation. Most proteins had the same denaturation patterns in the absence or presence of the drug, whereas target proteins with shifted thermal stability showed different amounts in the soluble fraction upon drug engagement. All proteins in the soluble fraction were conjugated with two different dyes containing N-hydroxysuccinimide (NHS) ester: Cy3-NHS for the vehicle-treated group as a negative control and Cy5-NHS for the drug-treated group. The dye-conjugated proteomes of both groups were mixed and separated by 2D gel electrophoresis (2-DE), and the ratio of Cy5 to Cy3 fluorescence signal of each protein spot was quantified by automated image analysis.

Proteins that did not undergo thermal stability shift by the drug appeared as yellow spots (additive signals of Cy3 and Cy5), whereas proteins that were thermally stabilized and destabilized by drug engagement appeared as red spots and green spots, respectively. Additionally, the unheated proteome was conjugated with Cy2-NHS, and the same amount of Cy2-conjugated proteome was added to each gel sample as an internal standard for inter-gel quantification. Therefore, the melting curves of each protein spot were obtained (FIG. 1).

Thermally shifted spots in TS-FITGE were considered to be potential target proteins and excised for identification by mass spectrometry.

Example 1

Preparation of Three Fluorescent Dyes for the Same Electrophoretic Mobility

To minimize deviations in mobility among Cy2-, Cy3-, and Cy5-conjugated proteins on 2D gels, we prepared charge- and mass-matched dyes. The synthesis procedures of each dye are below.

Synthesis of Cy2

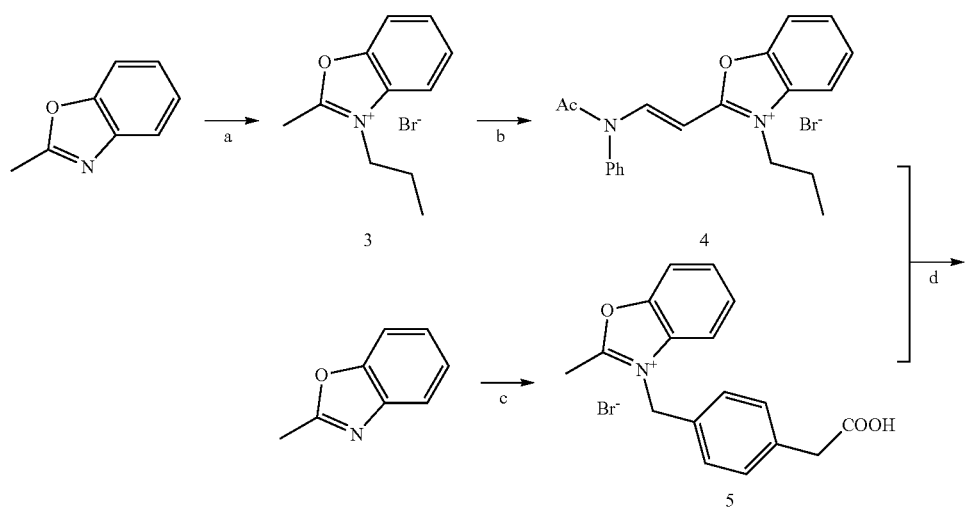

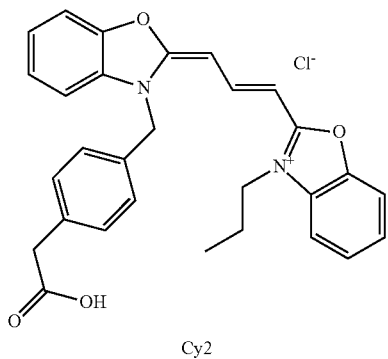

Cy2

Reagents and conditions: (a) A solution of n-propyl bromide (0.1 mmol, 1 equiv.) and 2-methylbenzoxazole (0.1 mmol, 1 equiv.) in 1,2-dichlorobenzene (10 mL) was stirred at 110° C. for 24 h. The reaction mixture was triturated with ether, and the precipitate was washed with ether to obtain desired product 3 as a white crystalline. (b) A solution of 3 (0.1 mmol, 1 equiv.) and N,N'-diphenylformamidine (0.1 mmol, 1.2 equiv.) in acetic anhydride (10 mL) was stirred at 120° C. for 30 min. The solvent was removed under reduced pressure, and the residue was purified by flash column chromatography with dichloromethane/methanol to obtain desired product 4 as a yellow crystalline. (c) A solution of 4-(bromomethyl)phenylacetic acid (0.1 mmol, 1 equiv.) and 2-methylbenzoxazole (0.1 mmol, 1 equiv.) in 1,2-dichlorobenzene (10 mL) was stirred at 110° C. for 24 h. The reaction mixture was triturated with ether, and the precipitate was washed with ether to obtain the desired product 5 as a yellow crystalline. (d) Triethylamine was added to a solution of 4 (0.1 mmol, 1 equiv.) and 5 (0.1 mmol, 1 equiv) in ethanol (10 mL), and stirred at 80° C. for 30 min. The solvent was removed under reduced pressure, and the residue was purified by flash column chromatography with dichloromethane/methanol to obtain desired product Cy2 as a deep yellow crystalline

Synthesis of Cy3

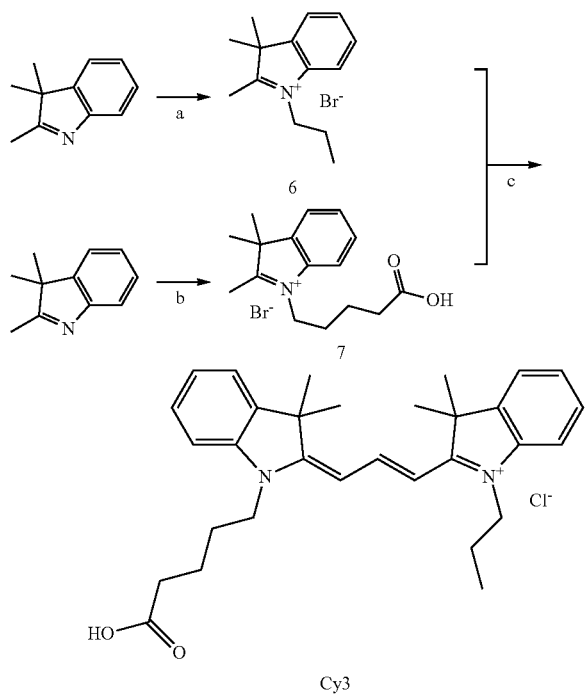

Reagents and conditions: (a) A solution of n-propyl bromide (0.1 mmol, 1 equiv.) and 2,3,3-trimethylindolenine (0.1 mmol, 1 equiv.) in nitromethane (10 mL) was stirred at 80° C. for 6 h. The reaction mixture was triturated with ether, and the precipitate was washed with ether to obtain desired product 6 as pink crystalline. (b) A solution of 5-bromovaleric acid (0.1 mmol, 1 equiv.) and 2,3,3-trimethylindolenine (0.1 mmol, 1 equiv.) in nitromethane (10 mL) was stirred at 80° C. for 6 h. The reaction mixture was triturated with ether, and the precipitate was washed with ether to obtain desired product 7 as violet crystalline. (c) A solution of 7 (0.1 mmol, 1 equiv.) and N,N'-diphenylformamidine (0.12 mmol, 1.2 equiv.) in acetic anhydride (10 mL) were stirred at 120° C. for 30 min. The reaction mixture was cooled to room temperature, then a solution of 6 in pyridine (10 mL) was added. The mixture was stirred at room temperature for 12 h. The solution was concentrated and dissolved in chloroform, and washed with water and 1N HCl aqueous solution. The organic layer was then dried with MgSO$_4$, filtered, evaporated, and purified by flash column chromatography with dichloromethane/methanol to obtain Cy3 as a deep pink crystalline.

Synthesis of Cy5

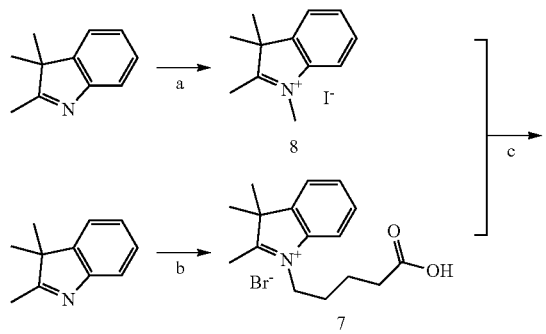

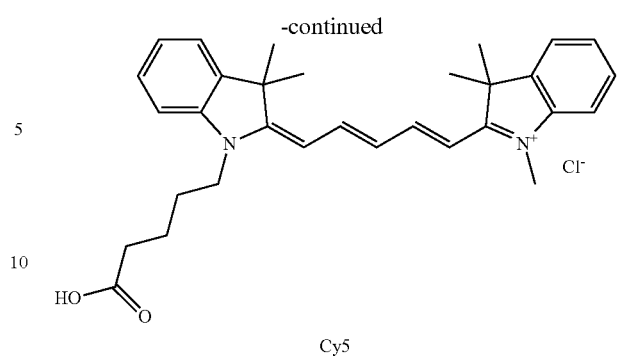

Reagents and conditions: (a) Iodomethane, nitromethane, r. t., 12 h. (b) Same as scheme (b) in the synthesis of Cy3. (c) A solution of 5 (0.1 mmol, 1 equiv.) and malondialdehyde bis(phenylimine) monohydrochloride (0.12 mmol, 1.2 equiv.) in acetic anhydride (10 mL) was stirred at 120° C. for 30 min. The reaction mixture was cooled to room temperature, then a solution of 8 in pyridine (10 mL) was added. The mixture was stirred at room temperature for 12 h. The solution was concentrated and dissolved in chloroform, and washed with water and 1N HCl aqueous solution. The organic layer was then dried with MgSO$_4$, filtered, evaporated, and purified by flash column chromatography with dichloromethane/methanol to obtain Cy5 as a deep blue crystalline.

Synthesis of Cy2, Cy3, Cy5-NHS ester

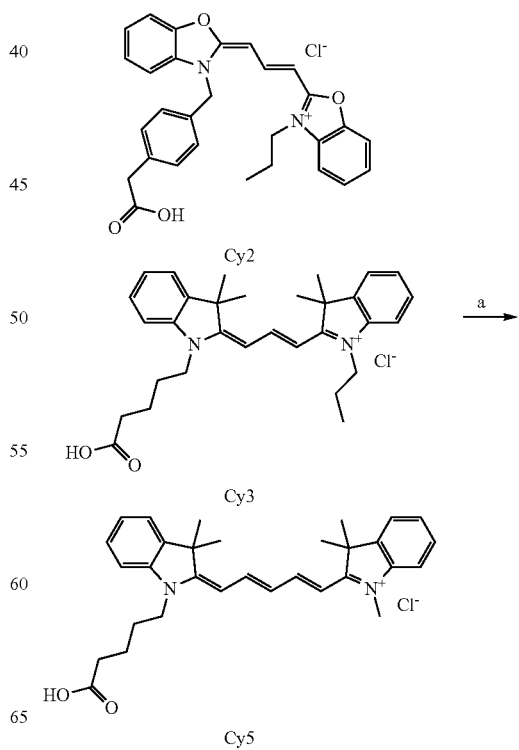

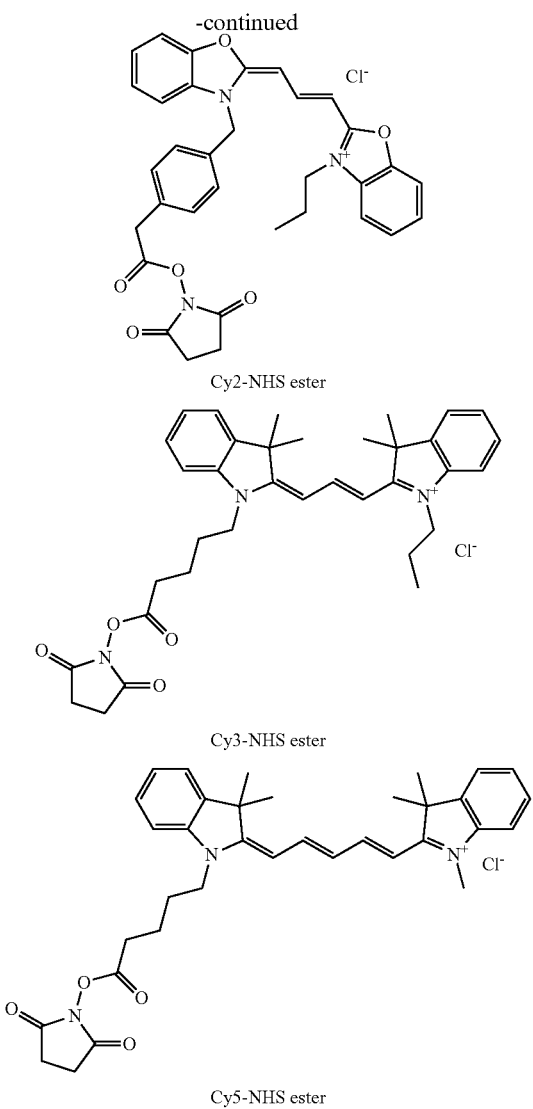

Reagents and conditions: (a)Pyridine (0.2 mL) and N,N'-disuccinimidyl carbonate (DSC, 0.15 mmol, 1.5 equiv.) was added to a solution of Cy2, Cy3, or Cy5 (0.1 mmol, 1.0 equiv.) in DMF (5 mL). The mixture was stirred at 60° C. for 2 h. The solvent was removed under reduced pressure, and the residue was purified by flash column chromatography with dichloromethane/methanol to obtain desired product Cy2-NHS ester, Cy3-NHS ester, or Cy5-NHS ester, respectively.

Figure 2:
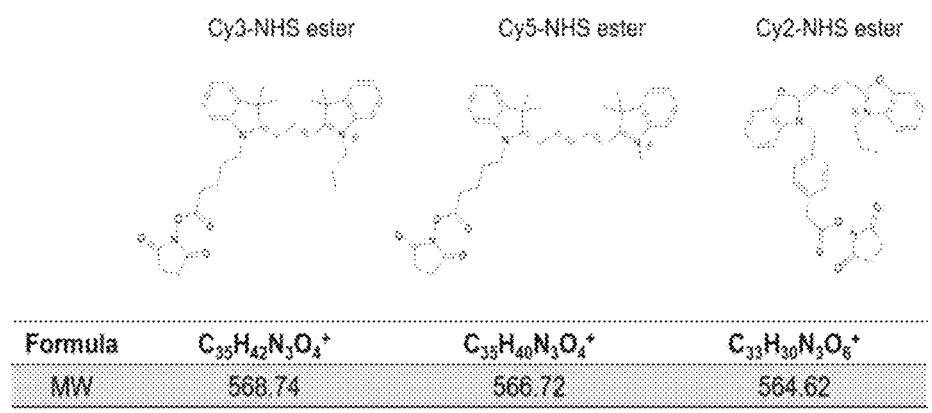
FIG. 2 shows a chemical structure, formula, and molecular weight of three fluorescent dyes (Cy3-NHS ester, Cy5-NHS ester, and Cy2-NHS ester).
Figure 3:
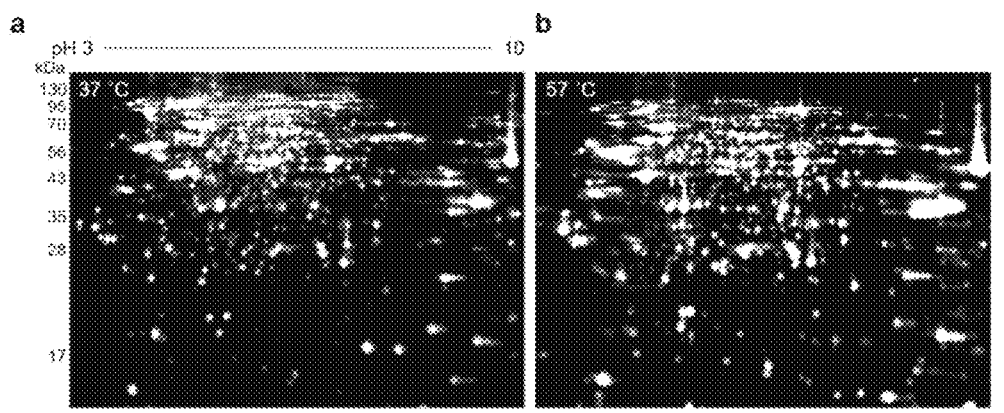
FIG. 3 is representative images showing the same mobility of proteomes conjugated with three different dyes. (a) Cy2, Cy3, and Cy5 signals were overlapped at the 37° C. gel, and most spots appeared as white color. (b) At 57° C., thermally unstable proteins were precipitated and removed from soluble fraction. Therefore, those spots were shown as blue color from unheated internal standard which was labelled with Cy2 dye.

All dyes had +1 charge and differed by only 2 Da from each other (FIG. 2). As the proteins conjugated with Cy2, Cy3, and Cy5 had the same mobility, most protein spots in the 37° C. gel appeared as white after merging (FIG. 3). At a higher temperature, thermally unstable proteins (proteins conjugated with Cy3 and Cy5) were denatured and disappeared. Therefore, these spots appeared as a blue color because of the unheated internal standard conjugated to Cy2 dye (FIG. 3b).

Example 2

Proof-of-Concept Target Identification Study With Methotrexate

Methotrexate was selected for the proof-of-concept study because its major target protein, dihydrofolate reductase (DHFR), was known to have a significantly large $T_m$ shift of 16° C. (Martinez Molina, D. et al., Science. 341, 84-87 (2013)). Among a series of 2D gels at various denaturing temperatures, nearly all protein spots in the 37° C. gel were yellow, while a distinct red spot was detected in the 53° C. gel (FIGS. 4a and 5). For quantitative analysis, the ratios of Cy5 to Cy3 signals of all protein spots in the 53° C. gel were calculated and presented in a box plot (FIG. 4b).

Figure 4:
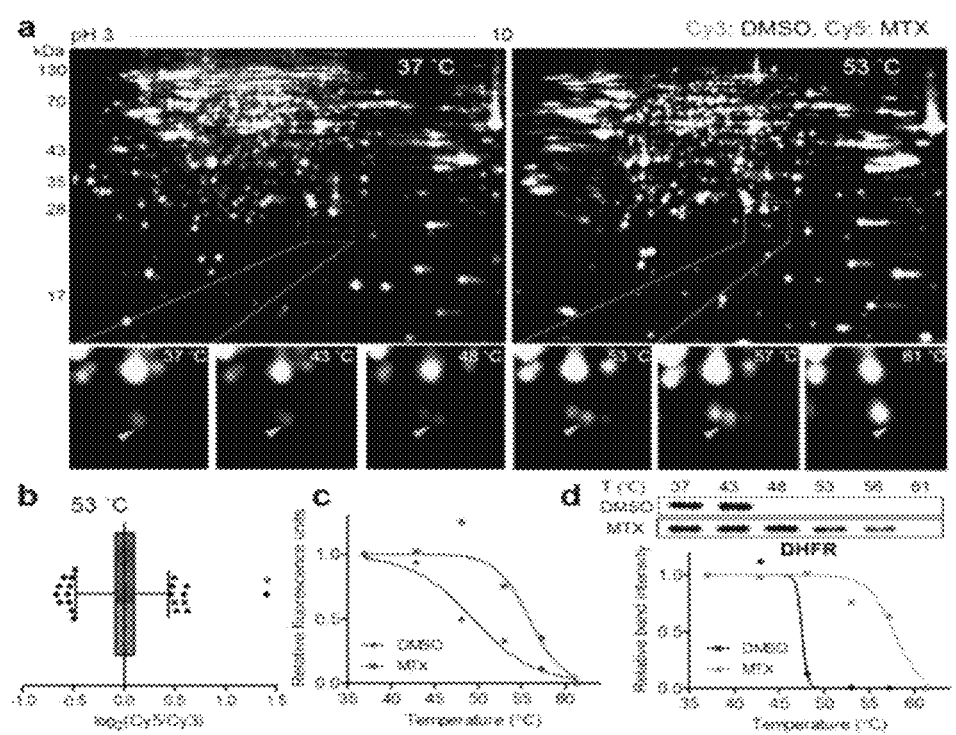
FIG. 4 shows unbiased identification of the target protein of methotrexate (MTX). (a) Representative images from TS-FITGE experiment. Images of Cy3 channel (green, proteome treated with DMSO) and Cy5 channel (red, proteome treated with MTX) were overlaid. (b) Box plot showing the distribution of Cy5/Cy3 fluorescence ratio for each spot in the 53° C. gel. The whiskers indicate 1-99 percentiles. The spot denoted by a triangle in (a) is indicated by a red arrow. (c) Melting curves showing a denaturation pattern of the indicated spot in (b). (d) Immunoblot from cellular thermal shift assay with dihydrofolate reductase (DHFR) antibody.
Figure 5:
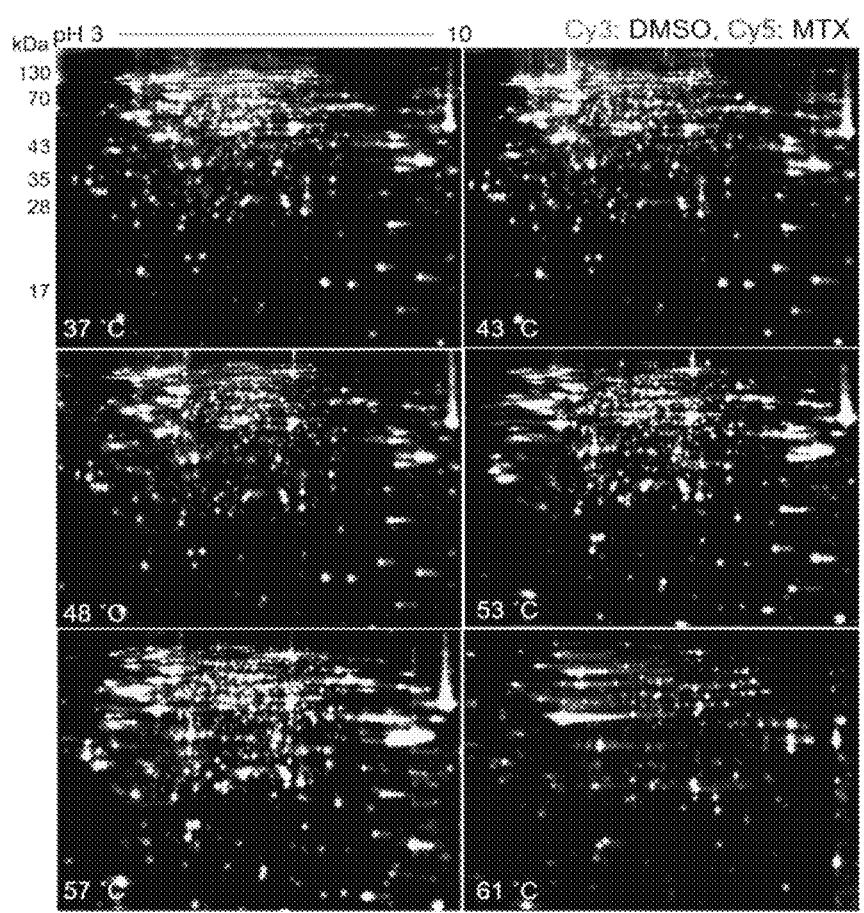
FIG. 5 shows whole gel images from TS-FITGE experiments with methotrexate (MTX).

As expected, the red spot indiated in FIG. 4a showed the highest ratio (indicated by an arrow in FIG. 4b), suggesting that this spot had significantly different Cy5 and Cy3 fluorescence signals. The melting curve of the spot was plotted across a range of temperatures using Cy2 signals as internal standards and revealed a shift of the sigmoidal curve, indicating an increase in Tm for the potential target protein of methotrexate (FIG. 4c).

Finally, the spot was excised and analyzed by LC-MS/MS, which revealed DHFR as the target protein (Table 1). Western blot analysis using a monoclonal DHFR antibody revealed a comparable thermal shift pattern to the pattern determined by TS-FITGE.

Figure 6:
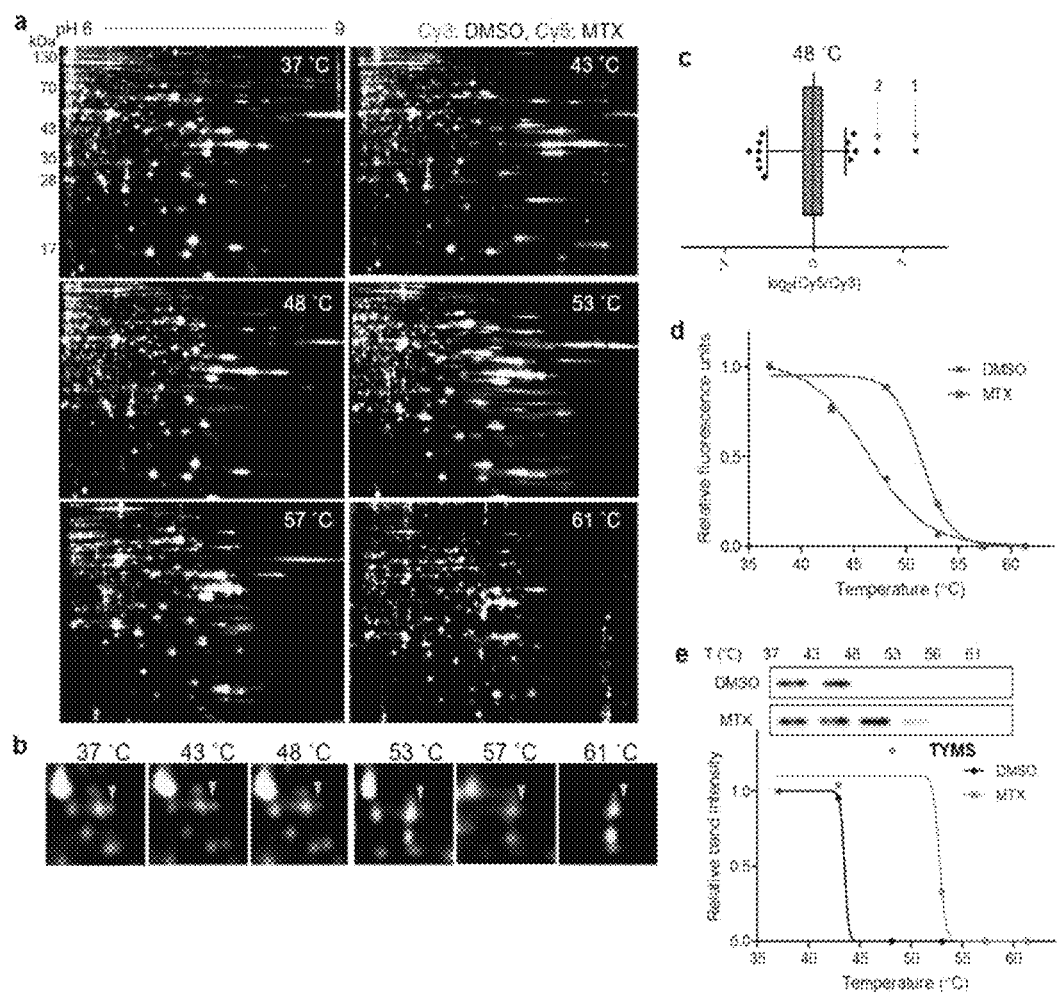
FIG. 6 shows identification of thymidylate synthase as another target protein of methotrexate (MTX). (a) Whole gel images from TS-FITGE experiments with MTX. Strip gels of pH gradient 6 to 9 were used for better resolution in basic pH range. (b) Enlarged images of the region indicated by white box in (a). (c) Box plot showing the distribution of Cy5/Cy3 signal ratio for each spot in the 48° C. gel. The whiskers indicate 1-99 percentiles. The spot pointed by a triangle in (b) is indicated by a red arrow 1. Red arrow 2 is the spot of dihydrofolate reductase (DHFR). (d) Melting curves showing the denaturation pattern of the arrowed spot 1 in (c). (e) Immunoblot from cellular thermal shift assay with thymidylate synthase (TYMS) antibody.

Moreover, thymidylate synthase, another target protein of methotrexate, was also identified as a thermal-stabilized spot showing a marked red color in the 48° C. gel, where the quantitative fluorescence difference of the thymidylate synthase spot was highest followed by the DHFR spot (FIG. 6 and Table 1).

As a result, we confirmed that TS-FITGE based on the thermal stability shift is a feasible and efficient strategy for unbiased target identification in live cells.

TABLE 1

Figure 7:
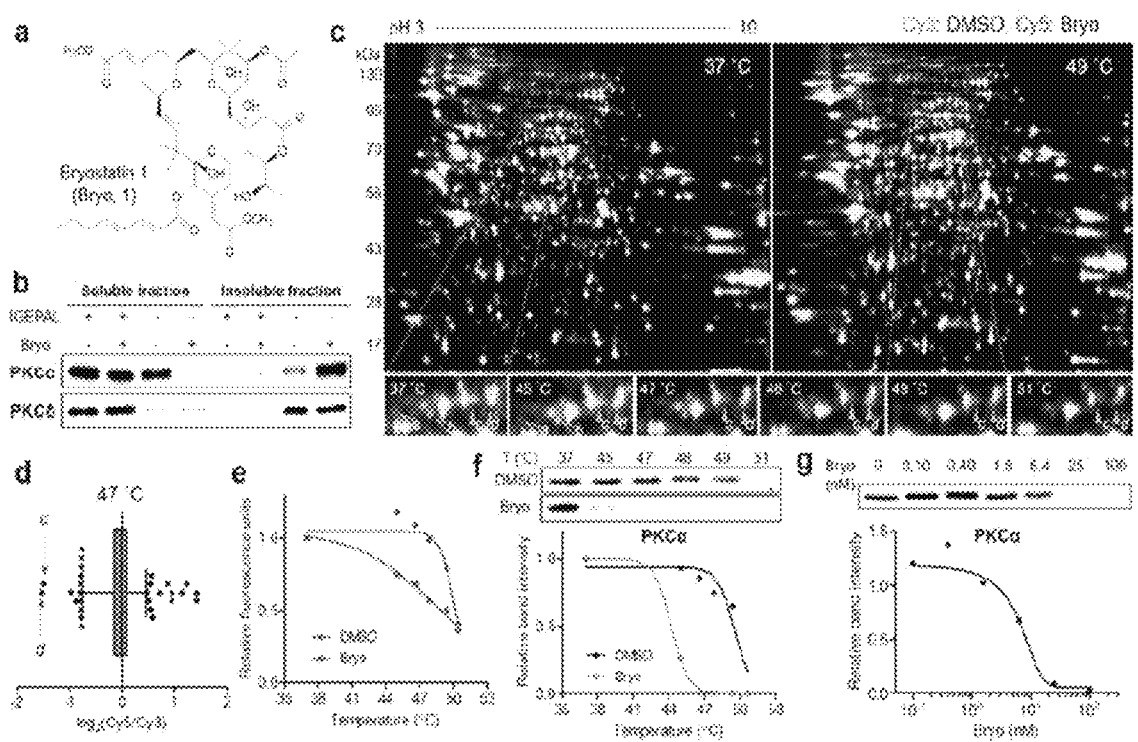
FIG. 7 shows thermal destabilization of the membrane-anchored target protein of bryostatin 1. (a) Chemical structure of bryostatin 1 (Bryo). (b) Translocation of PKC isozymes by bryostatin land effect of IGEPAL CA-630 on solubilization of PKCs. (c) Representative images from TS-FITGE experiment treating bryostatin 1. (d) Box plot showing the distribution of Cy5/Cy3 signal ratio for each spot in the 47° C. gel. The whiskers indicate 1-99 percentiles. (e) Melting curves showing denaturation pattern of the spots indicated in (d). (f) Immunoblot from cellular thermal shift assay with PKCα antibody. (g) An isothermal (48° C.) dose—response curve confirming thermal destabilization of PKCα by bryostatin 1.

| Compound | Protein spot | Match to | Molecular Weight | Mascot Score | Queries matched | Sequence Coverage (%) | Protein |
|---|---|---|---|---|---|---|---|
| Methotrexate | FIG. 4a | DRY_HUMAN | 21439 | 533 | 79 | 82 | Dihydrofolate reductase |
| | FIG. 6b | TYSY_HUMAN | 35693 | 527 | 19 | 37 | Thymidylate synthase |
| | | PRPS1_HUMAN | 34812 | 224 | 11 | 38 | Ribose-phosphate pyrophosphokinase 1 |
| Bryostatin 1 | FIG. 7c, a | ELMO1_HUMAN | 83776 | 210 | 19 | 21 | Engulfment and cell motility protein 1 |
| | FIG. 7c, b | ELMO1_HUMAN | 83776 | 287 | 27 | 30 | Engulfment and cell motility protein 1 |
| | FIG. 7c, c | MCM7_HUMAN | 81257 | 615 | 29 | 39 | DNA replication licensing factor MCM7 |
| | | KPCA_HUMAN | 76714 | 220 | 10 | 18 | Protein kinase C alpha type |
| | | SYTC_HUMAN | 83382 | 183 | 12 | 20 | Threonyl tRNA synthetase, cytoplasmic |

TABLE 1-continued

Figures 13A, 13B, 13C:
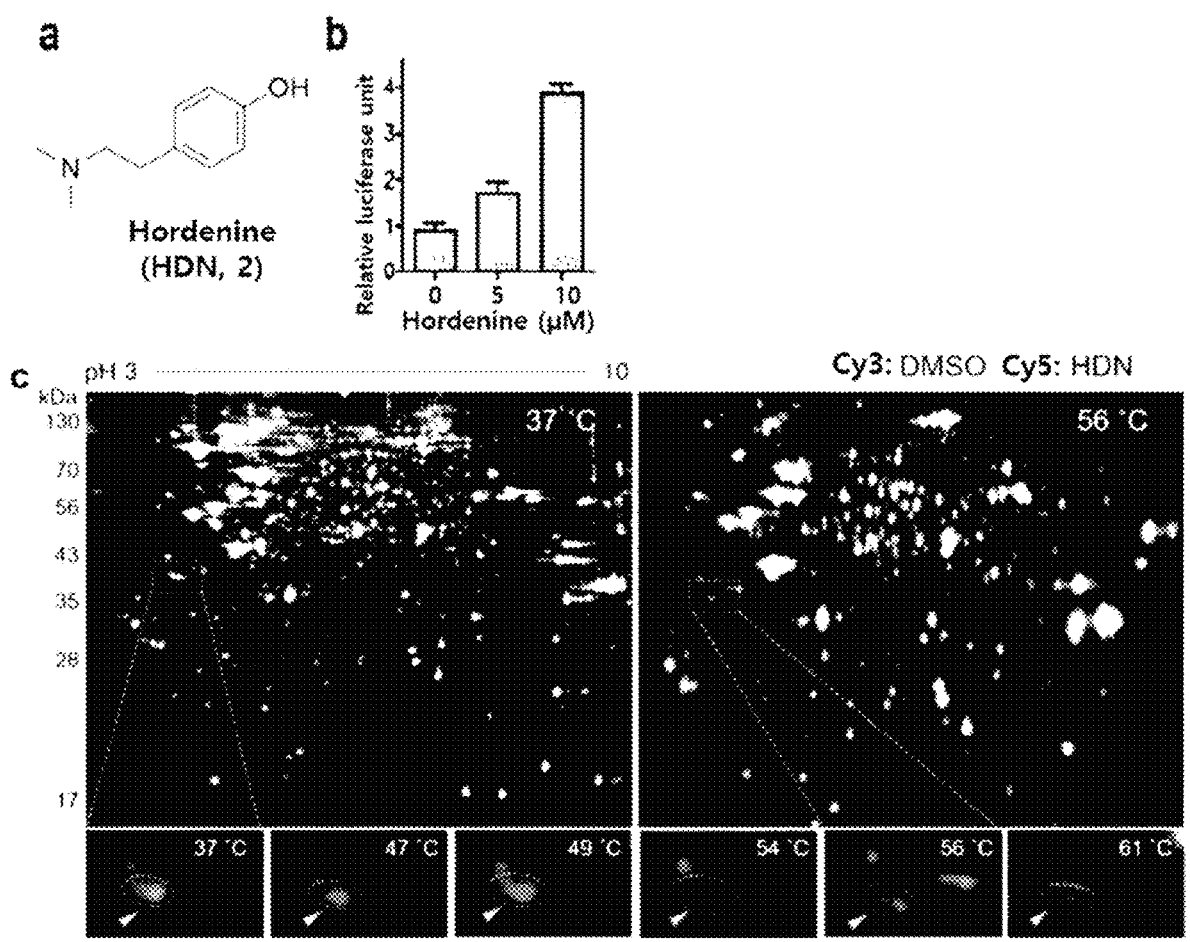
FIG. 13 shows Identification of the novel target protein of hordenine. (a) Chemical structure of hordenine (N,N-dimethyltyramine, HDN). (b) Upregulational effect of HDN on in vitro translation assay measured by luciferase reporter gene product. Data are presented as the mean±SEM (n=2). (c) Representative images from the TS-FITGE experiment. Images of Cy3 channel (green, proteome treated with DMSO) and Cy5 channel (red, proteome treated with HDN) were overlaid. (d) Box plot showing distribution of Cy5/Cy3 fluorescence ratio for each spot in the 53° C. gel. The whiskers indicate 1-99 percentiles. The spot pointed with a triangle in (c) was indicated by a red arrow. (e) Melting curves showing denaturation pattern of the spot indicated in (d). (f) Immunoblot from cellular thermal shift assay with HDNantibody. Data are presented as the mean±SEM (n=4). (g) Sensorgrams from surface plasmon resonance assay showing the binding kinetics of HDN (1.56-37.5 µM) to immobilized NPM. Inset in a right and upper part shows the steady-state response against various concentrations of HDN. (h) Immunoblot with NPM antibody showing depletion of NPM by anti-NPM bound protein G beads. (i) Decreased efficacy of NPMon translational upregulation after NPM depletion. Data are presented as the mean±SEM (n=3). *P<0.05 by paired student's t-test.

| Compound | Protein spot | Match to | Molecular Weight | Mascot Score | Queries matched | Sequence Coverage (%) | Protein |
|---|---|---|---|---|---|---|---|
| | FIG. 7c, d | KPCA_HUMAN | 76714 | 307 | 16 | 28 | Protein kinase C alpha type |
| | | SYTC_HUMAN | 83382 | 135 | 11 | 18 | Threonyl tRNA synthetase, cytoplasmic |
| | FIG. 9b, e | MCM7_HUMAN | 81257 | 276 | 10 | 18 | DNA replication licensing factor MCM7 |
| | | KPCA_HUMAN | 76714 | 132 | 7 | 12 | Protein kinase C alpha type |
| | | EFG1_HUMAN | 83418 | 108 | 5 | 8 | Elongation factor G 1, mitochondrial precursor |
| | FIG. 9b, f | DC1I2_HUMAN | 71412 | 395 | 15 | 32 | Cytoplasmic dynein 1 intermediate chain 2 |
| | | GRP78_HUMAN | 72288 | 119 | 9 | 16 | 78 kDa glucose-regulated protein precursor |
| | FIG. 9b, g | DC1I2_HUMAN | 71412 | 489 | 12 | 26 | Cytoplasmic dynein 1 intermediate chain 2 |
| | | GRP78_HUMAN | 7228 | 195 | 13 | 24 | 78 kDa glucose-regulated protein precursor |
| | FIG. 9b, h | HNRPK_HUMAN | 50944 | 488 | 25 | 57 | Heterogeneous nuclear ribonucleoprotein K |
| | FIG. 9b, i | HNRPK_HUMAN | 50944 | 405 | 23 | 40 | Heterogeneous nuclear ribonucleoprotein K |
| | | PGTA_HUMAN | 65030 | 144 | 11 | 22 | Geranylgeranyl transferase type-2 alpha subunit |
| | | HDAC1_HUMAN | 55068 | 126 | 4 | 12 | Histone deacetylase 1 |
| | FIG. 9b, j | HNRPK_HUMAN | 50944 | 519 | 25 | 52 | Heterogeneous nuclear ribonucleoprotein K |
| | | PGTA_HUMAN | 65030 | 399 | 15 | 29 | Geranylgeranyl transferase type-2 alpha subunit |
| | | CH60_HUMAN | 61016 | 354 | 17 | 30 | 60 kDa heat shock protein, mitochondrial precursor |
| | | TCPQ_HUMAN | 59583 | 173 | 10 | 21 | T-complex protein 1 subunit theta |
| | | TCPE_HUMAN | 59633 | 153 | 14 | 33 | T-complex protein 1 subunit epsilon |
| Hordenine | FIG. 13c | NPM_HUMAN | 32555 | 5562 | 175 | 87 | Nucleophosmin |
| | | EF1D_HUMAN | 31103 | 1847 | 40 | 77 | Elongation factor 1-delta |
| | | SET_HUMAN | 33469 | 1039 | 47 | 48 | Protein SET |
| | | TTC1_HUMAN | 33505 | 888 | 45 | 75 | Tetratricopeptide repeat protein 1 |
| | | RSSA_HUMAN | 32833 | 347 | 11 | 29 | 40S ribosomal protein SA |
| | | HS90B_HUMAN | 83212 | 295 | 11 | 14 | Heat shock protein HSP 90-beta |
| | | HDGF_HUMAN | 26772 | 265 | 9 | 51 | Hepatoma-derived growth factor |
| | | VA0D_HUMAN | 40303 | 223 | 12 | 28 | Vacuolar ATP synthase subunit d |

Example 3

Identification of Membrane-Anchored Target Proteins of Bryostatin 1

To confirm the usefulness of the TS-FITGE method, we identified the target protein of a complex natural product, bryostatin 1. Bryostatins were first isolated from marine *Bugula neritina* and showed potent anticancer activity, synergistic chemotherapeutic activity, and memory-enhancing activity (Ruan et al., *Curr. Med. Chem.* 19, 2652-2664 (2012)). After the structure of bryostatin 1 was elucidated in 1982, its 58-step total synthesis was reported in 2011 (Keck et al., *J. Am. Chem. Soc.* 133, 744-747 (2011)). Therefore, bryostatin 1 is an example of a complex natural product for which it is difficult to synthesize appropriately functionalized probes for other target identification methods (FIG. 7a). Furthermore, bryostatins are known to modulate protein kinase Cs(PKCs) to translocate, anchor to the plasma membrane, and phosphorylate substrate proteins, which play important roles in cellular signaling processes (Sun et al., *CNS Drug Rev.* 12, 1-8 (2006)).

Figure 8:
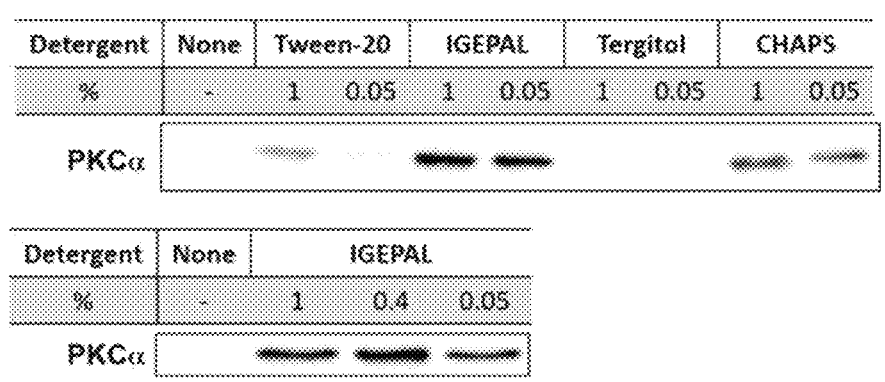
FIG. 8 shows the effect of detergent on solubilization of PKCs. (a) Optimization of the detergent condition in the lysis buffer using PKCα as a representative of PKCs for the initial screening. The amount of PKCα in the soluble fraction upon 1-h treatment with bryostatin 1 was measured by western blot. IGEPAL CA-630 most effectively solubilized PKCα. 0.4% (v/v) was better than 0.05% and similar to 1% for PKCα solubilization. (b) Translocation of PKCμ and PKCζ upon 1-h treatment with bryostatin 1 and the effect of 0.4% of IGEPAL CA-630 on their solubilization.
Figure 8:
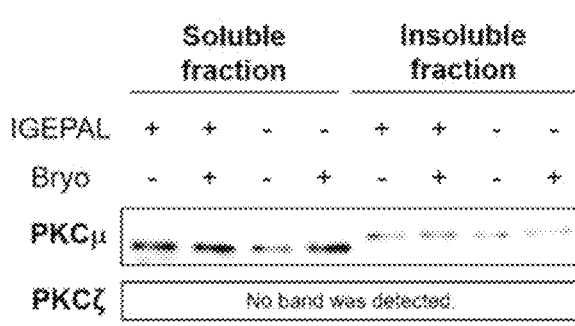

To investigate whether membrane-anchored proteins are compatible with our TS-FITGE method, we first screened the effect of detergents on solubilizing the PKCs by western blotting and optimized the lysis conditions in phosphate-buffered saline containing 0.4% (v/v) of IGEPAL CA-630, a nonionic and nondenaturing detergent, among various other detergents (FIG. 8a). As shown in FIG. 7b, PKCα was mainly present in the soluble fraction before bryostatin treatment, but moved to insoluble fraction following treatment with bryostatin in lysis buffer without a mild detergent. In the presence of 0.4% of IGEPAL CA-630, however, PKCα remained in the soluble fraction even after bryostatin treatment. The location of PKCδ was not affected by bryostatin treatment, but a nonionic detergent was essential for solubilization in both cases (FIG. 7b). Solubilization of other PKC isozymes was not affected by bryostatin and detergent (FIG. 8b). Thus, we concluded that 0.4% of IGEPAL CA-630 was required to globally solubilize PKCs and detect thermal stability shifts in the soluble fraction.

Figure 9:
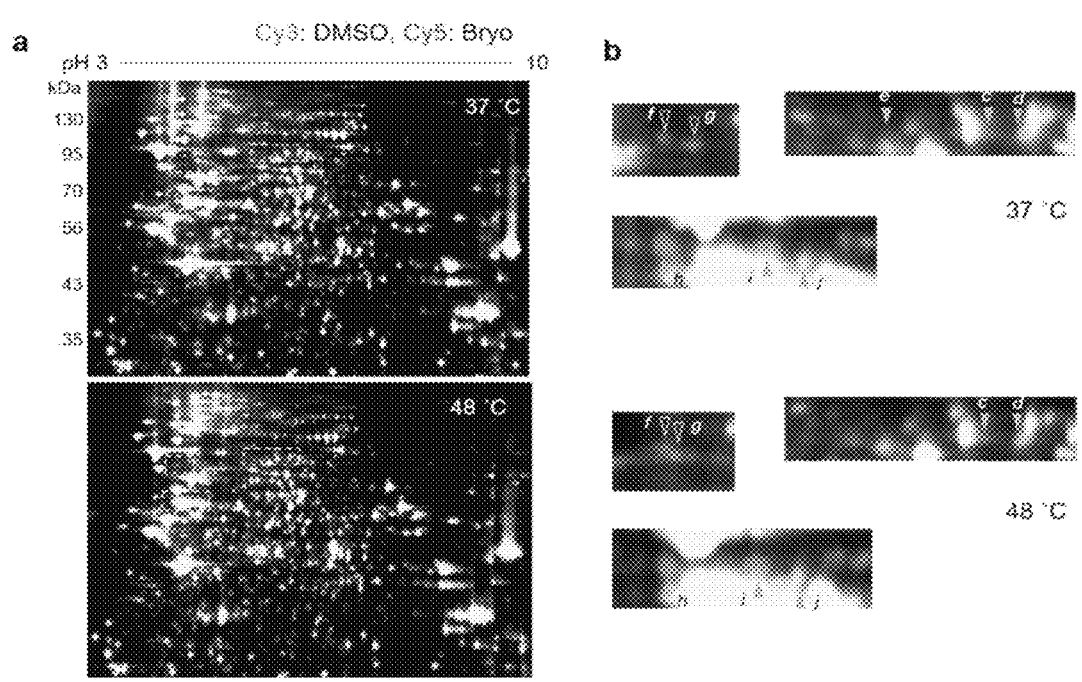
FIG. 9 shows appearance of red and green spots upon treatment of bryostatin 1 without heat denaturation. (a) Representative images from the TS-FITGE experiment upon treatment with bryostatin 1 for 75 min. (b) Enlarged images of the regions indicated by white boxes in (a).
Figure 10:
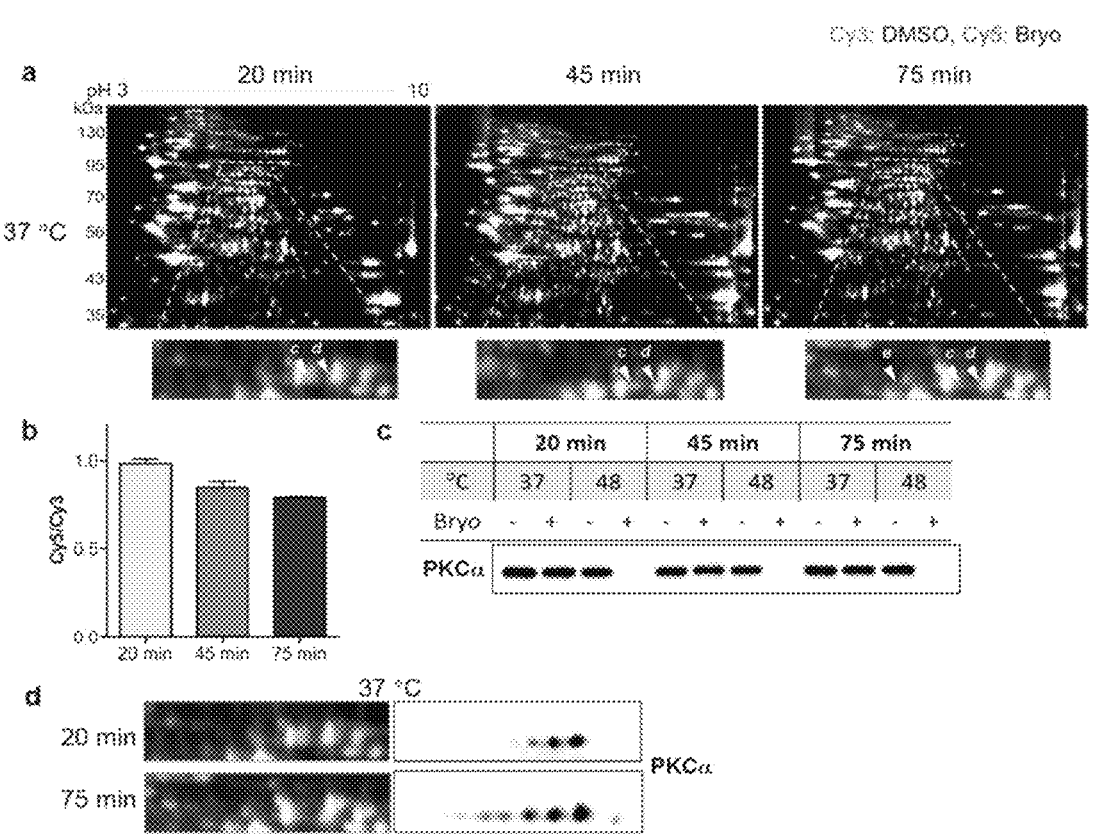
FIG. 10 shows effect of the treatment time on protein spot shift. (a) 2D gel analysis of color change upon treatment of bryostatin 1 without thermal denaturation. As the treatment time decreased, protein e disappeared, and protein c and d became yellow. (b) The quantitative ratio of Cy5 to Cy3 signals of the protein d. (c) Immunoblot with PKCα antibody on a 1D gel to compare the total amount of PKCα. The total amounts of PKCα were identical regardless of treatment time at 37° C. (d) Immunoblot with PKCα antibody on 2D gels. Treatment for 75 min induced the appearance of additional PKCα spots. The additional spots appeared as red color, and the remaining spots became green on the fluorescence image

Next, we performed TS-FITGE experiment with bryostatin to monitor the thermal denaturation pattern of the cellular proteome using the optimized lysis conditions. Interestingly, several spots appeared as red or green not only in the heated samples but also in the unheated (37° C.) sample, indicating that the color difference in these spots did not originate from thermal shifting (FIG. 7c, protein a and b; FIG. 9, protein c, d, e, f g, h, i, and j). In addition, most red and green spots appeared horizontally next to each other in a pairwise arrangement. This phenomenon is a typical post-translational modification (PTM) pattern observed in 2-DE. Thus, we considered that these spots were not thermally shifted target proteins, but rather posttranslationally modified downstream substrates after drug engagement at 37° C. The red and green protein spots caused by PTM may be reduced simply by shortening the duration of drug treatment not to allow sufficient time for PTM to occur. As expected, the green spots c and d at 37° C. became yellowish, while the red spots including e disappeared as the treatment time decreased (FIGS. 10a and 10b). After identification of protein spots c, d, and e as PKCα (Table 1), we performed western blot analysis using a PKCα antibody. The total amount of PKCα at 37° C. was identical in the 1D gel, but PKCα was separated to horizontal red and green spots in the 2D gel with increasing treatment time of bryostatin 1 (FIGS. 10c and 10d). These results were all consistent with the interpretation that the red and green spots in the 37° C. gel resulted from PTMs.

Figure 11:
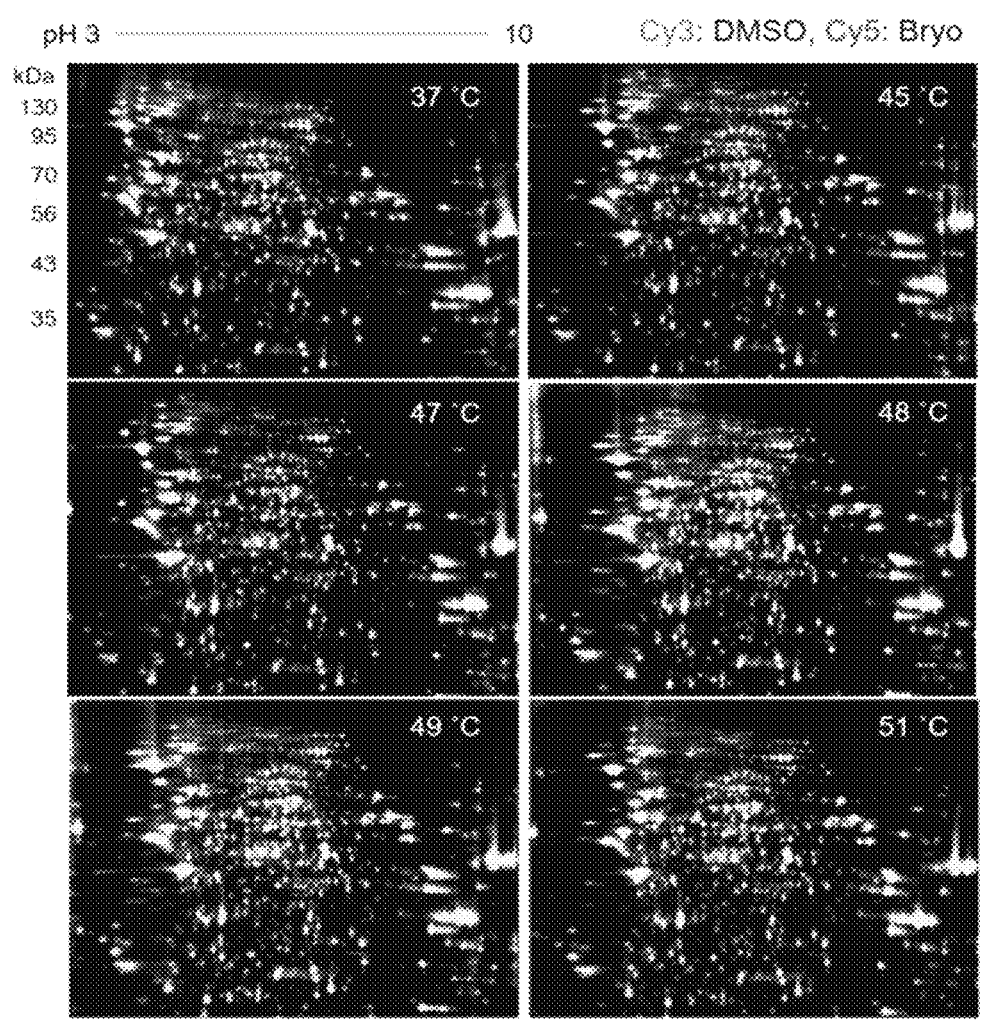
FIG. 11 shows whole gel images from TS-FITGE experiments upon treatment with bryostatin 1 for 20 min.
Figure 12:
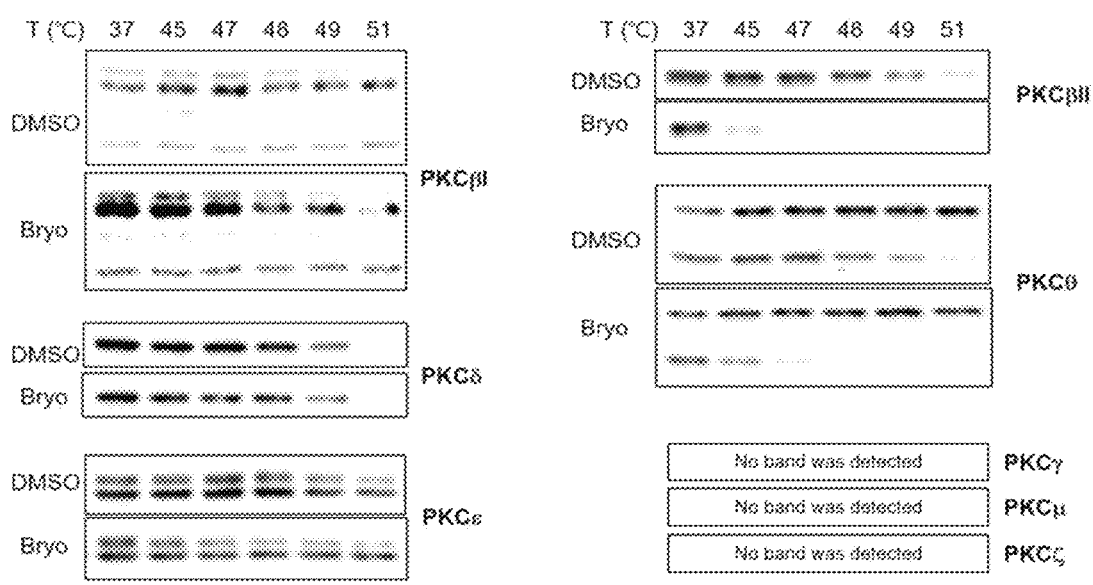
FIG. 12 shows CETSA analysis against PKC isozymes. PKCβ and PKCθ showed thermal destabilization, while the others did not.

After 20 min treatment with bryostatin 1, we observed distinct green spots in the heated sample, but not in the unheated sample, indicating thermal destabilization upon target engagement (FIG. 7c, protein c and d; FIG. 11). These spots showed the lowest ratio for Cy5 to Cy3 signals in the 47° C. gel, suggesting that significant thermal destabilization occurred (FIG. 7d). Spots with the highest Cy5/Cy3 signal ratios were ruled out because they were also red color in the unheated gel, and thus their signal differences were not caused by thermal stability shift, but rather by PTM. Both spot c and d showed temperature-dependent thermal destabilization patterns, and the melting curve of protein d is presented in FIG. 7e. Mass spectrometry revealed the protein identity of both spot c and d as PKCα, the target of bryostatin 1 (Table 1). Generally, a target protein is known as being thermally stabilized by drug engagement (Niesen et al., *Nat. Protoc.* 2, 2212-2221 (2007)). We performed CETSA to confirm the thermal destabilization of PKCα by bryostatin 1, which firmly confirmed the thermal destabilization of PKCα (FIG. 7f). Additionally, an isothermal dose—response curve at 48° C. revealed dose-dependent thermal destabilization of PKCα (FIG. 7g), supporting our observations. We performed CETSA for other PKC isozymes because bryostatin 1 is known to bind to other PKC isozymes (Kazanietz et al., *Mol. Pharmacol.* 46, 374-379 (1994)). PKCβII and PKCθ showed thermal destabilization, while PKCβI, PKCδ, and PKCε showed no significant thermal stability shifts, and the anticipated bands of PKCγ, PKCμ, and PKCζ were not detectable (FIGS. 8b and 12).

Example 4

Identification of a Novel Target Protein of Hordenine Using TS-FITGE

Finally, we applied our TS-FITGE method to a bioactive small natural product that has a simple chemical structure lacking room for chemical modification. Hordenine, N,N-dimethyltyramine (FIG. 13a), is an alkaloid found in several plants, particularly sprouting barley (Smith et al., *Phytochemistry.* 16, 9-18 (1977)). Hordenine has several bioactivities such as the stimulation of gastrin release in rats, the inhibition of norepinephrine uptake in vasa deferentia, and the increases in respiratory and heart rates when intravenously injected into horses (Frank et al., *Equine Vet. J.* 22, 437-441 (1991)).

From screening of small-molecule libraries to identify compounds affecting in vitro protein translation, hordenine was found to increase the translation of the luciferase reporter gene (FIG. 13b). However, we found no previous reports examining the biological activity of hordenine and its binding partners related to protein translation.

Figures 13D, 13E:
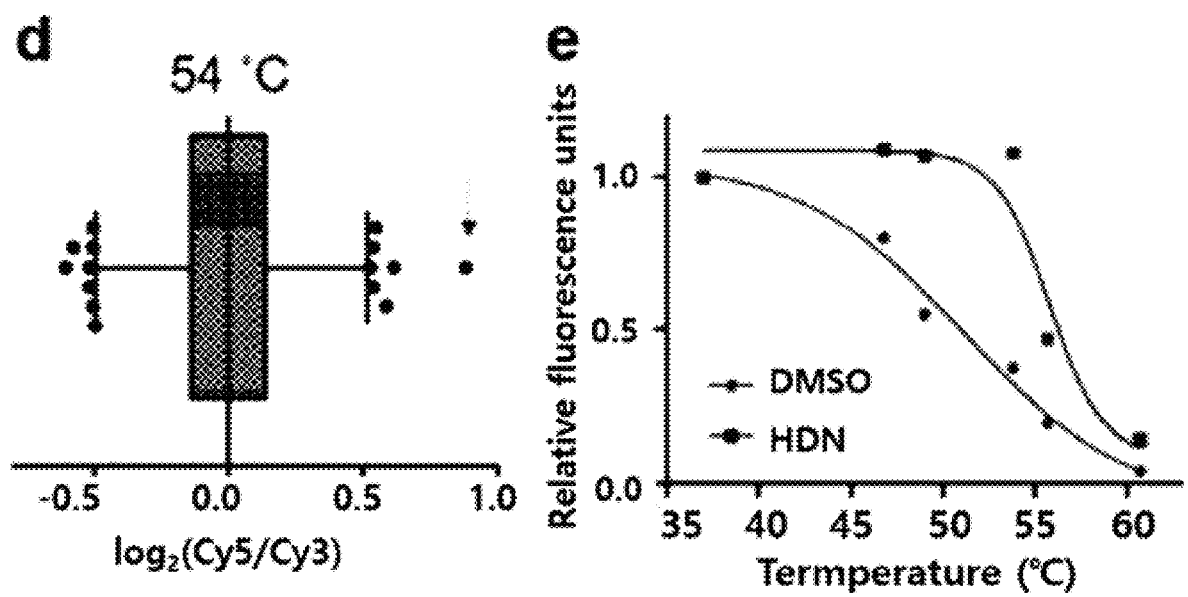
Figures 13F, 13G:
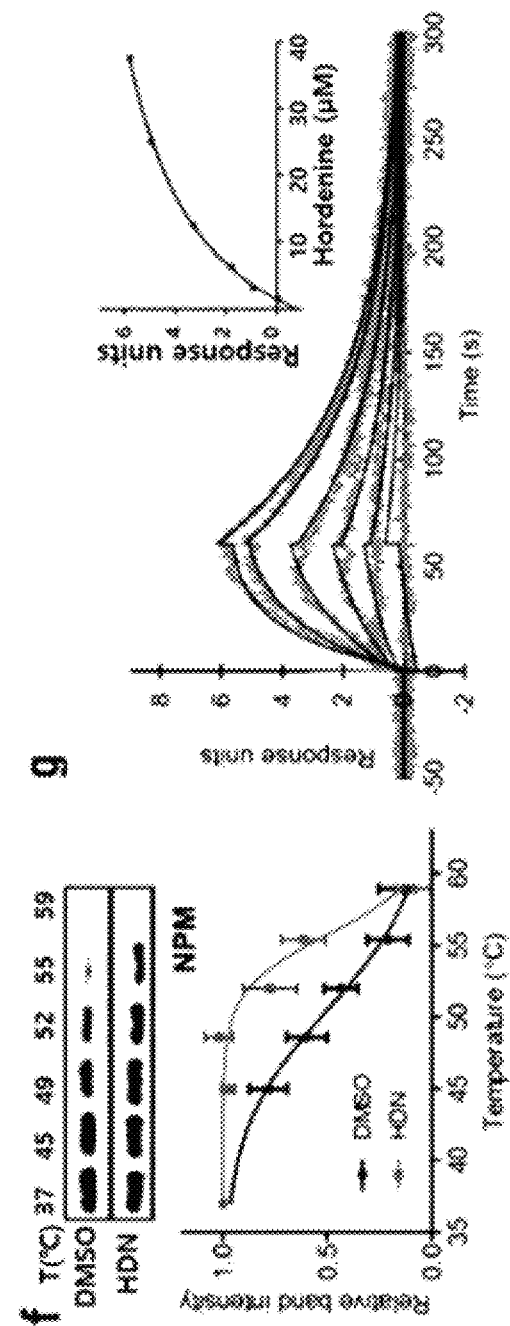
Figure 14:
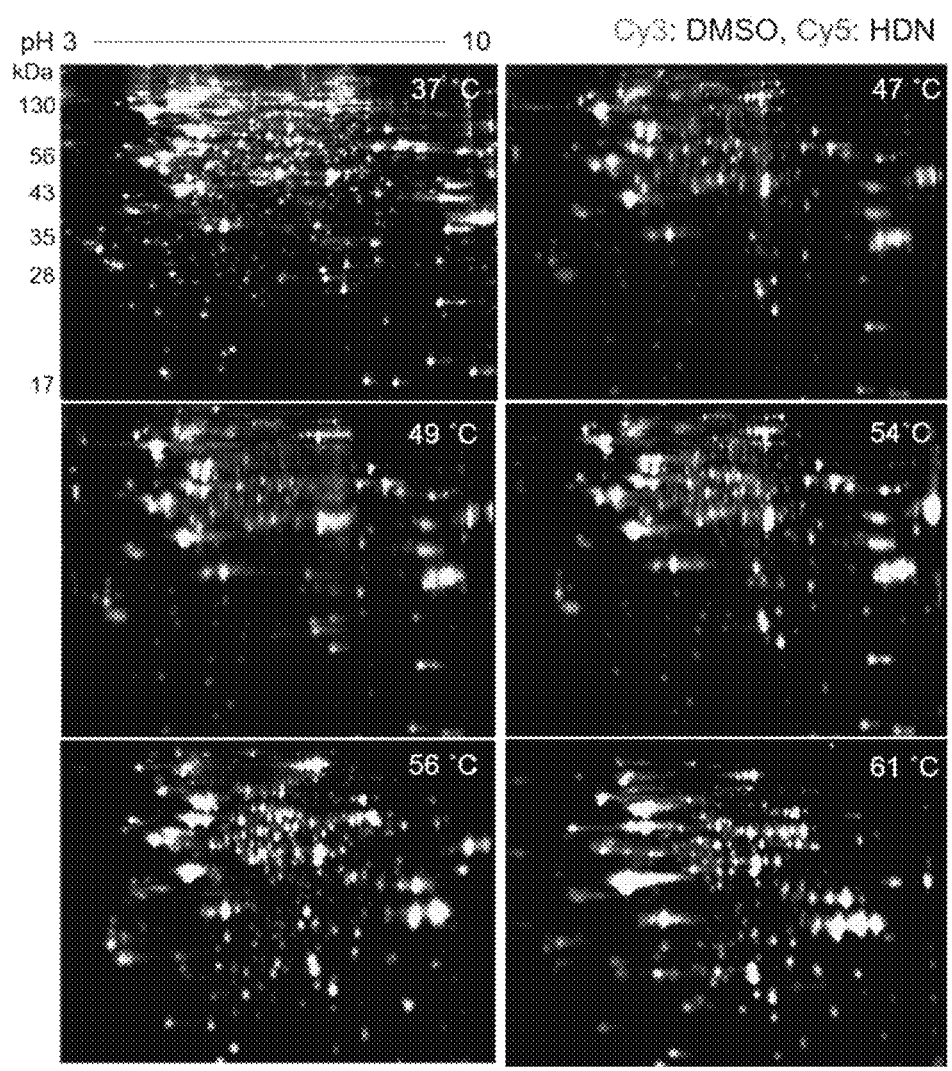
FIG. 14 shows whole gel images from TS-FITGE experiments upon treatment with hordenine.
Figure 15:
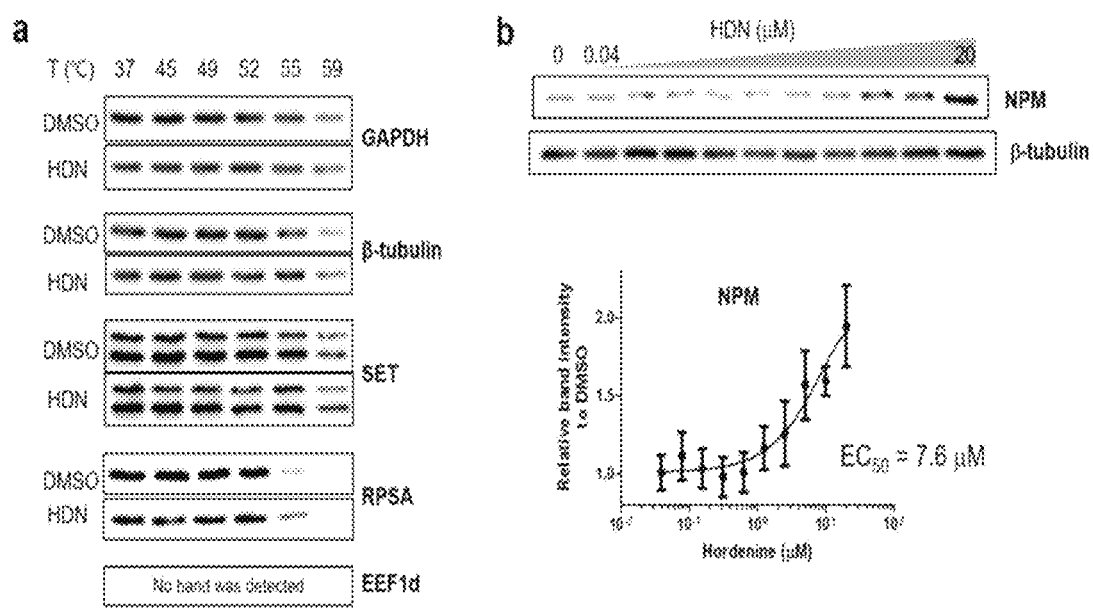
FIG. 15 shows immunoblot analysis to test the target protein showing thermal stabilization. (a) Cellular thermal shift assay on SET, RPSA, and EEF1d in comparison with a control protein, GAPDH and β-tubulin. (b) Isothermal dose-response analysis of NPM and β-tubulin at 53° C. NPM protein showed a dose-dependent thermal stabilization by HDN.
Figure 16:
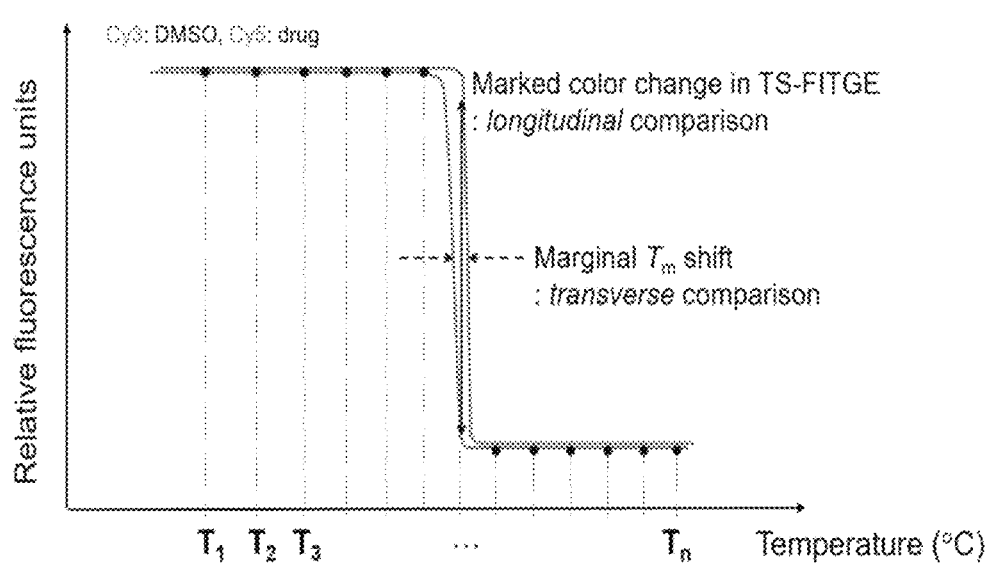
FIG. 16 shows description of the analysis procedure in the TS-FITGE. As the fluorescence difference at each temperature is directly compared in TS-FITGE, marked color change can be detected at a certain temperature even if Tm shift is marginal. The certain temperaure point can be captured by increasing the number of gels.

We performed TS-FITGE using HEK293T cells to identify target proteins of hordenine. A reddish spot was detected (FIGS. 13c and 14) wherein the spot showed the highest Cy5/Cy3 ratio in the 54° C. gel (FIG. 13d). This spot was quantified over a range of temperatures to plot the sigmoidal melting curve (FIG. 13e), and the spot was excised for LC-MS/MS analysis to obtain a list of target candidates (Table 1). To determine the binding partner, we performed CETSA of nucleophosmin (NPM), elongation factor 1-delta (EEF1D), protein SET (SET), and 40S ribosomal protein SA (RPSA), which are related to protein translation (FIGS. 13f and 15a).

NPM showed significant thermal stabilization compared to β-tubulin and GAPDH, while the other candidate proteins did not. Dose-dependent thermal stabilization of NPM by hordenine was confirmed by the isothermal dose—response graph at 53° C. with an EC50 value of 7.6 mM (FIG. 15b). To confirm the direct binding of hordenine to NPM, we conducted surface plasmon resonance analysis, which clearly showed a concentration-dependent response of the conventional one-to-one binding pattern with a $K_D$ value of 13.6 mM (FIG. 13g).

Figures 13H, 13I:
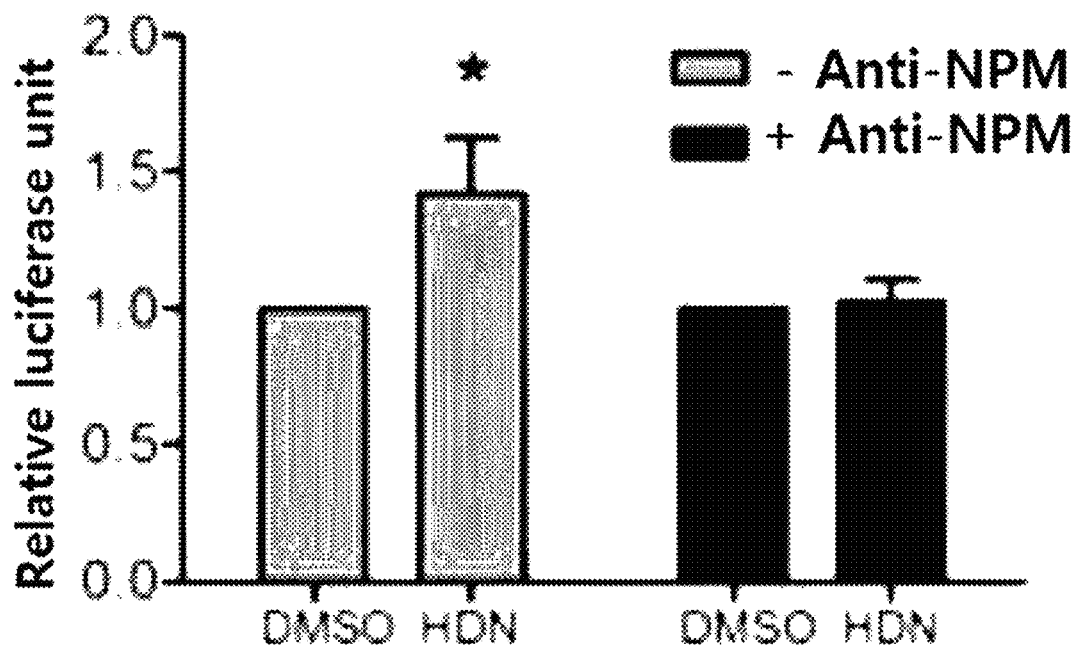

To determine whether the upregulation of in vitro protein translation was caused by the functional modulation of NPM by hordenine, we conducted the functional validation via a loss-of-function study by depleting NPM from the in vitro translation system. Briefly, NPM antibody bound to protein G on agarose beads was incubated with the in vitro translation system to scavenge NPM. After removing the agarose beads, the remaining NPM in the solution was reduced, as observed in the western blotting results (FIG. 13h). The original upregulating efficacy of hordenine on luciferase gene translation was diminished by 72.7% after NPM depletion (FIG. 13i), validating that hordenine upregulated in vitro protein translation of the luciferase reporter gene by directly regulating NPM.

Methods Used in the Examples

Chemicals and reagents—All chemicals including methotrexate, bryostatin 1, hordenine, and branched octylphenoxy poly(ethyleneoxy)ethanol (IGEPAL CA-630) were purchased from Sigma-Aldrich. Cell culture reagents including media, fetal bovine serum (FBS), and antibiotic-antimycotic solution were from Gibco [Life technologies]. Dulbecco's phosphate-buffered saline (DPBS) was purchased from Welgene. Complete protease inhibitor cocktail (EDTA-free) was from Roche.

Cell culture—HEK293T and Jurkat clone E6-1 cells were purchased from Korea cell line bank. HEK293T cells were cultured in DMEM supplemented with 10% (v/v) FBS and 1% (v/v) antibiotic-antimycotic solution. Jurkat cells were cultured in RPMI 1640 media supplemented with 10% (v/v) FBS and 1% (v/v) antibiotic-antimycotic solution. Cells were maintained at 37° C. in humidified 5% $CO_2$ incubator.

Preparation of cell extract—Jurkat cell was used for bryostatin 1 and HEK293T cell for methotrexate and hordenine. HEK293T cells were harvested with trypsin/EDTA solution and resuspended in a conical tube before compound treatment. Methotrexate was incubated with HEK293T cells at 10 μM for 3 h, and hordenine with HEK293T cells at 20 μM for 3 h. After the compound treatment, cells were aliquoted, heated to a range of temperature for 3 min, and cooled to 25° C. for 3 min. The heated cells were harvested, washed with PBS, and resuspended with lysis buffer (PBS supplemented with protease inhibitor cocktail). The cell suspension was freeze-thawed three times with liquid nitrogen for cell lysis. Soluble fraction was separated from the cell lysate following centrifugation at 20,000 g for 20 min at 4° C. Procedures for isothermal dose-response (ITDR) analysis was identical with the above-mentioned procedures except that cells were treated with various compound concentrations and heated at a fixed temperature.

Western blot—The soluble fraction was mixed with 5×Laemmli buffer followed by heating at 95° C. for 5 min. Proteins were separated by SDS-PAGE and transferred to PVDF membranes. The membranes were in tris-buffered saline with Tween-20 (TBST) including 2% BSA for 1 h at 4° C., and incubated with primary antibodies (anti-DHFR [ab133546, abcam], anti-TYMS [3766, Cell signaling], anti-PKCα [2056, Cell signaling], anti-PKCβI [ab195039, abcam], anti-PKCβII [ab32026, abcam], anti-PKCγ [402 ab131222, abcam], anti-PKCδ [9616, Cell signaling], anti-PKCε [ab124806, abcam], anti-PKCμ [2052, Cell signaling], anti-PKCθ [ab110728, abcam], anti-PKCζ [9368, Cell signaling], anti-NPM [ab52644, abcam], anti-RPSA [ab133645, abcam], anti-SET [ab176567, abcam], anti-EEF1D [ab88868, abcam], anti-GAPDH [2118, Cell signaling], and anti-β-tubulin [2146, Cell signaling])) overnight. The membrane was then washed with TBST and incubated with secondary antibodies (anti-rabbit IgG, HRP linked [7074, Cell signaling]) for 1 h at room temperature. The membranes were developed with Amersham ECL prime western blotting detection reagent [GE Healthcare], and detected by ChemiDoc [Bio-Rad]. The relative band intensities to 37° C. was calculated within each of drug-treated group and control group each for the CETSA curves. For ITDR curves, the relative band intensities to DMSO group was calculated. Data analysis and sigmoidal curve fitting were done by GraphPad Prism 5.

2D gel electrophoresis—Protein concentration of the soluble fraction of cell extract was quantified with Bio-Rad protein assay. Acetone was added to 50 μg of the protein and incubated at −20° C. for 1 h. The mixture was centrifuged at 20,000g for 20 min at 4° C. Supernatant was discarded, and the pellet was washed with cold acetone twice. The residual pellet was sonicated for resuspension with 10 μl of conjugation buffer (30 mM Tris-HCl (pH 8.6), 2 M thiourea, 7 M urea, 4% CHAPS (w/v)). 1 μl of 0.4 mM Cy3-NHS or Cy5-NHS were mixed to the resuspended proteins and incubated at 4° C. for 50 min. 320 μg of unheated sample for internal standard was precipitated, resuspended with 64 μl of the conjugation buffer, and mixed with 6.4 μl of Cy2-NHS. After the conjugation, cold acetone was added and incubated at −20° C. for 1 h. The mixture was centrifuged at 20,000g for 20 min at 4° C. Supernatant was discarded, and the pellet was washed with cold acetone twice. Heated samples were sonicated for resuspension with 50 μl of rehydration buffer (7 M urea, 2 M thiourea, 2% CHAPS (w/v), 40 mM DTT, and 1% IPG buffer) and 320 μl of standard samples . 50 μl of compound-treated group (conjugated with Cy5) and DMSO-treated group (conjugated with Cy3) were mixed; 50 μl of the unheated sample (conjugated with Cy2) was added for internal standard. Total 150 μg (50 μg for Cy2, Cy3, and Cy5 each) of proteins were loaded in a 24-cm Immobiline Drystrip gel [GE Healthcare] which was rehydrated for 10 h, and isoelectric focusing was done by Ettan IPGphor 3 [GE Healthcare]. The proteins in the strip gel were separated by Ettan DALTsix electrophoresis system [GE Healthcare], the gel was scanned with Typhoon Trio [GE Healthcare].

Gel image analysis—Fluorescence signals from Cy2, Cy3, and Cy5 were quantified by DeCyder 2D software, ver. 7.2 [GE Healthcare]. Signal ratio values of Cy5 to Cy3 were normalized, so that the modal peak of the logarithm value of the ratio was set to be zero. The data were presented in a box-and-whisker diagram, and outliers were considered as thermally shifted spots. Used as internal standards for inter-gel analysis, Cy2 signal matched the location of each spot across all gels, and the relative amounts of Cy3 and Cy5 signals to Cy2 signal were calculated to plot melting curves. Data analysis and sigmoidal curve fitting were done by GraphPad Prism 5.

Mass spectrometry—The protein spots from silver-stained gel were excised and destained followed by in gel trypsin digestion. The extracts were evaporated in SpeedVac and then dissolved in 10% acetonitrile containing 0.1% formic acid. The resulting proteins were desalted with trap column (internal diameter 180 μm×20 mm, Symmetry C18) cartridge and separated on a C18 reversed-phase 75 μm internal diameter×200 mm analytical column (1.7 μm particle size, BEH130 C18, Waters) with integrated electrospray ionization PicoTip (±10 μm internal diameter, New Objective) using nanoAcquity UPLC-ESI-QTOF/MS [SYNAPT G2-Si HDMS, Waters]. The acquired data were converted to .pkl files with Protein Lynx Global Server and used to query the SwissProt database using MASCOT search.

In vitro protein translation—TNT quick coupled transcription/translation system [Promega] was used for in vitro translation. TNT Quick Master Mix and T7 luciferase control DNA were mixed according to the manufacturer's protocol, and incubated with compounds at 30° C. for 1 h. After the addition of Luciferase assay reagent [Promega], luminescence from the control luciferase product was read by Synergy HT [BioTek] to measure the effect of compounds on protein translation.

Nucleophosmin depletion for functional validation—Protein G sepharose beads [Sigma] were washed with PBS and incubated with anti-NPM antibody at 4° C. for 2 h. Unbound antibodies were washed away. The anti-NPM bound Protein G beads were mixed with TNT Quick Master Mix and incubated at 4° C. for 2 h. The beads were removed by centrifugation, and the supernatant was incubated with T7 luciferase control DNA and 10 μM of hordenine at 30° C. for 1 h. Luminescence was read after the addition of Luciferase assay reagent.

Surface plasmon resonance assay—Binding kinetics were monitored by BIAcore T100 instrument [GE Healthcare]. Buffer condition of the human nucleophosmin full length protein [ab126664, abcam] was exchanged to PBS using 10K Amicon ultra centrifugal filter [Millipore]. The carboxyl group on CMS chip surface was activated by injection of a mixture of NHS and EDC to both flow cells 1 and 2. Nucleophosmin protein (36 μg/mL) in acetate buffer (pH 4.0) was injected to the flow cell 2 for 550 sec with flow rate of 5 μl/min. Ethanolamine-HCl was injected to both flow cells 1 and 2 for quenching. Final immobilization level reached 9,400 RU and 12,800 RU for two independent experiments. For binding study, various concentration (1.56 μM to 37.5 μM) of hordenine was injected for 60 sec with flow rate of 30 μl/min and dissociated with injection of the running buffer (PBS supplemented with 0.005% P20, and 2% DMSO) for 400 seconds. Data were analyzed by BIAcore T100 Evaluation software [GE Healthcare], and the sensorgram was fitted to the 1:1 binding model.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for identifying a target protein of a drug molecule, comprising the steps of:
    (a) preparing a mixture A comprising cell lysates or human-derived cells;
    (b) preparing a separate mixture B comprising (i) the same cell lysates or human-derived cells used in (a) and (ii) the drug molecule;
    (c) adjusting the temperature of the mixture A and the temperature of the mixture B to a same predetermined temperature sufficient to induce thermal denaturation;
    (d) mixing the mixture A at the predetermined temperature with a first fluorescent material containing N-hydroxysuccinimide (NHS) ester and having a first fluorescence wavelength and mixing the mixture B at the predetermined temperature with a second fluorescent material containing N-hydroxysuccinimide (NHS) ester and having a second fluorescence wavelength that is different from the first fluorescence wavelength so that a protein existed in a soluble fraction of the mixture A and a protein existed in a soluble fraction of the mixture B are labeled with the first and the second fluorescent materials, respectively;
    (e) mixing the mixture A and the mixture B as obtained in step (d) to prepare a mixture C;
    (f) performing an electrophoresis of the mixture C; and
    (g) analyzing a fluorescence wavelength of a protein spot shown in a gel by the electrophoresis of step (f) to confirm a protein showing thermal stability shift resulting from step (c).

2. The method according to claim 1, characterized in that the predetermined temperature of step (c) is in the range from 37 to 70° C.

3. The method according to claim 1, characterized in further comprising the step of plotting a melting curve graph for each protein spot in step (g).

4. The method according to claim 1, characterized in that the drug molecule of step (b) is a bioactive molecule.

5. The method according to claim 1, characterized in that the protein obtained in step (g) is a membrane-anchored protein.

6. The method according to claim 1, characterized in that in the thermal stability shift of step (g), the protein existed in the mixture B is thermally stabilized by engagement with the drug molecule.

7. The method according to claim 6, characterized in that the protein is nucleophosmin (NPM) and the drug molecule is hordenine as a bioactive molecule.

8. The method according to claim 1, characterized in that in the thermal stability shift of step (g), the protein existed in mixture B is thermally destabilized by engagement with the drug molecule.

9. The method according to claim 8, characterized in that the protein is protein kinase Cα (PKCα) and the drug molecule is bryostatin 1 as a bioactive molecule.

10. The method according to claim 1, characterized in that the first and second fluorescent materials of step (d) are, independently, at least one selected from the group consisting of Cy2, Cy3, Cy5, fluorescein, Alexafluor488, R6G, HEX, AlexaFluor32, TAMRA, AlexaFluor546, EtBr, SYPRO Ruby, and Blue FAM.

11. The method according to claim 10, characterized in that in step (d), the first fluorescent material mixed with the mixture A is Cy3 and the second fluorescent material mixed with the mixture B is Cy5.

12. The method according to claim 1, characterized in that the analysis of the fluorescence wavelength of step (g) consists of the analysis of the ratio between the fluorescence wavelength generated from the first fluorescent material labelled on the protein existed in the soluble fraction of the mixture A and the fluorescence wavelength generated from the second fluorescent material labelled on the protein existed in the soluble fraction of the mixture B.

13. The method according to claim 1, characterized in that the electrophoresis of step (f) is two-dimensional gel electrophoresis.

* * * * *